(12) United States Patent
Engler et al.

(10) Patent No.: US 7,142,634 B2
(45) Date of Patent: Nov. 28, 2006

(54) RADIATION FIELD DETECTION

(75) Inventors: Mark J. Engler, Lexington, MA (US);
Mark J. Rivard, Hopkinton, MA (US)

(73) Assignee: New England Medical Center Hospitals, Inc., Boston, MA (US)

( * ) Notice: Subject to any disclaimer, the term of this patent is extended or adjusted under 35 U.S.C. 154(b) by 0 days.

(21) Appl. No.: 10/767,024

(22) Filed: Jan. 29, 2004

(65) Prior Publication Data
US 2005/0109939 A1    May 26, 2005

Related U.S. Application Data

(60) Provisional application No. 60/443,475, filed on Jan. 29, 2003.

(51) Int. Cl.
*A61N 5/10*    (2006.01)

(52) U.S. Cl. ....................... 378/65

(58) Field of Classification Search ............... 378/65
See application file for complete search history.

(56) References Cited

U.S. PATENT DOCUMENTS

| | | | |
|---|---|---|---|
| 4,147,936 A * | 4/1979 | Eickel | 378/22 |
| 4,163,240 A * | 7/1979 | Swinehart et al. | 257/430 |
| 5,430,308 A * | 7/1995 | Feichtner et al. | 250/580 |
| 5,621,214 A * | 4/1997 | Sofield | 250/375 |
| 5,661,773 A * | 8/1997 | Swerdloff et al. | 378/65 |
| 5,754,622 A * | 5/1998 | Hughes | 378/65 |
| 6,225,622 B1 * | 5/2001 | Navarro | 250/252.1 |
| 6,345,114 B1 * | 2/2002 | Mackie et al. | 382/132 |
| 6,546,070 B1 * | 4/2003 | Francke | 378/51 |
| 6,675,116 B1 | 1/2004 | Ritt | 702/104 |
| 6,783,275 B1 * | 8/2004 | Ghelmansarai | 378/206 |
| 6,853,702 B1 * | 2/2005 | Renner | 378/65 |
| 2003/0174808 A1 * | 9/2003 | Hughes et al. | 378/65 |
| 2004/0096033 A1 * | 5/2004 | Seppi et al. | 378/65 |

OTHER PUBLICATIONS

Tsai, et al., *J. Applied Clin. Med. Physics.*, 3(2):135-153 (2002).

* cited by examiner

*Primary Examiner*—Edward J. Glick
*Assistant Examiner*—Thomas R Artman
(74) *Attorney, Agent, or Firm*—Ingrid A. Beattie; Mintz, Levin, Cohn, Ferris, Glovsky and Popeo, P.C.; Shane H. Hunter

(57) ABSTRACT

A radiation field detection system, for use with a radiating device, includes a radiation detector configured to receive radiation and to provide radiation strength indicia of amounts of radiation received, a positioning mechanism connected to the radiation detector and configured to physically move the radiation detector, and a processor coupled to the positioning mechanism and coupled to the radiation detector to receive the radiation strength indicia, the processor being configured to: actuate the positioning mechanism to move the radiation detector to desired locations within a radiation field produced by the radiating device; analyze the radiation strength indicia from the radiation detector; correlate positions of the radiation detector with corresponding amounts of received radiation; determine a first location of maximum detected radiation; and determine a first relationship between the first location of maximum detected radiation and a second location of maximum radiation.

24 Claims, 13 Drawing Sheets

RADIATION FIELD DETECTION

CROSS-REFERENCE TO RELATED ACTIONS

This application claims the benefit of U.S. Provisional Application No. 60/443,475 filed Jan. 29, 2003.

FIELD OF THE INVENTION

The invention relates to radiation therapy and more particularly to determining and possibly using information regarding actual radiation distributions provided by radiating devices.

BACKGROUND OF THE INVENTION

Radiation therapy is a non-invasive medical treatment involving radiating one or more portions of a patient, such as neoplastic tissue, with high doses of radiation at one or more extremely precise locations. The radiation is delivered to focus high doses within the target tissue while attempting to minimize dose to surrounding normal tissues. Radiation therapy includes radiosurgery, including stereotaxic radiosurgery (SRS), that provides a form of non-invasive surgery that allows doctors to treat medical conditions. Examples of such conditions include malignant lesions, intracranial tumors, and various forms of cancers. In radiosurgery, neoplastic tissue such as a lesion or tumor existing in a patient's body is exposed to (i.e., irradiated with) focused radiation, such as collimated gamma radiation, delivered from a radiating device. Typically, the radiating device applies doses of radiation at prescribed strengths to a target area in order to inhibit the growth of the tissue in that area by altering the molecular structure of cells that form the tissue.

Included in radiation therapy, is a technology referred to as intensity modulated radiation therapy (IMRT). IMRT itself includes the use of proton radiation (intensity modulated proton therapy, or IMPT) and other particulate radiation. Typically, IMRT involves the use of a special multi-leaf collimator and high power computers to customize dose distributions to the specification of not only minimal dose volume relationships in targets but also maximal dose volume relationships required to spare surrounding normal tissues and organs from adverse effects. Part of this technology, known as inverse planning, involves the radiation oncologist entering a comprehensive prescription into a workstation with parallel processing computers to calculate, or optimize, the radiation intensity distributions needed to fulfill the prescription.

Several different persons are involved in providing radiation therapy to patients, including an oncologist, a physicist, and a therapist. The radiation oncologist, or dosimetrist, is a physician whose job it is to determine treatment for patients. The oncologist is certified and authorized to approve radiation therapy plans. To develop a radiation plan, the oncologist uses information regarding the patient and works with a qualified medical physicist to determine the therapy to apply to a patient. The oncologist uses the desired therapy in conjunction with computerized determinations of what radiation distributions that a radiating device can provide to determine a dosimetry/radiation plan for the patient to treat the target areas while limiting radiation to healthy tissue. The qualified medical physicist is someone familiar with therapeutic radiological physics, a.k.a. radiation oncology physics, and helps the oncologist appreciate with radiation therapies (e.g., radiation distributions) are available. The physicist is also responsible for calibrating the radiating device and performing quality assurance to help ensure that patients are being treated as intended. The physicist further works with the radiation therapist to plan the actual application of radiation to the patient. The radiation therapist, or operator, is the person that is licensed to use a radiating device on a patient and is responsible for implementing the radiation plan developed by the physicist and oncologist.

SUMMARY OF THE INVENTION

In general, in an aspect, the invention provides a radiation field detection system for use with a radiating device, the detection system including a radiation detector configured to receive radiation and to provide radiation strength indicia of amounts of radiation received, a positioning mechanism connected to the radiation detector and configured to physically move the radiation detector, and a processor coupled to the positioning mechanism and coupled to the radiation detector to receive the radiation strength indicia, the processor being configured to: actuate the positioning mechanism to move the radiation detector to desired locations within a radiation field produced by the radiating device; analyze the radiation strength indicia from the radiation detector; correlate positions of the radiation detector with corresponding amounts of received radiation; determine a first location of maximum detected radiation; and determine a first relationship between the first location of maximum detected radiation and a second location of maximum radiation.

Implementations of the invention may include one or more of the following features. The detection system further includes an output port configured to be coupled to a controller that determines an excitation arrangement for the radiating device, wherein the processor is further configured to provide an indication of the first relationship to the output port for conveyance to the controller. The second location of maximum radiation is one of (1) an expected location of maximum radiation and (2) a determined location of maximum radiation detected under a second radiation condition that is different than a first radiation condition in effect when the radiation was detected leading to the determination of the first location. The second radiation condition is a different angle of application of radiation by the radiating device, with the radiating device being a linear accelerator.

Implementations of the invention may also include one or more of the following features. The processor is further configured to determine a first magnitude of maximum detected radiation and to determine a second relationship between the first magnitude of maximum detected radiation and a second magnitude of maximum radiation. The detection system further includes an output port configured to be coupled to a controller that determines an excitation arrangement for the radiating device, wherein the processor is further configured to provide an indication of the magnitude relation to the output port for conveyance to the controller. The second magnitude of maximum radiation is one of (1) an expected magnitude of maximum radiation and (2) a determined magnitude of maximum radiation detected under a second radiation condition that is different than a first radiation condition in effect when the radiation was detected leading to the determination of the first location. The second radiation condition is a different angle of application of radiation by the radiating device, with the radiating device being a linear accelerator.

Implementations of the invention may also include one or more of the following features. The radiation detector is an ionization chamber. The radiation detector is a silicon diode detector that has a detection volume of less than about 0.2 mm$^3$. The positioning mechanism is configured to move the radiation detector three-dimensionally.

In general, in another aspect, the invention provides a radiation field detection system for use with a radiating device, the detection system including an ionization chamber radiation detector configured to receive radiation and to provide, in real time, radiation strength indicia of amounts of radiation received, a positioning mechanism connected to the radiation detector and configured to physically move the radiation detector, and a processor coupled to the positioning mechanism and coupled to the radiation detector to receive the radiation strength indicia, the processor being configured to: actuate the positioning mechanism to move the radiation detector to a desired location within a radiation field produced by the radiating device; analyze the radiation strength indicia from the radiation detector in real time; correlate positions of the radiation detector with corresponding amounts of received radiation in real time; and determine, in real time, a location of maximum detected radiation.

Implementations of the invention may include one or more of the following features. The processor is configured to correlate the positions of the radiation detector with corresponding amounts of detected radiation as information regarding the positions and the corresponding amounts of radiation becomes available. The ionization chamber is a silicon diode ionization chamber that has a detection volume of less than about 0.2 mm$^3$. The detection system further includes an output port configured to be coupled to a controller that determines an excitation arrangement for the radiating device, wherein the processor is further configured to provide an indication of the location of the maximum detected radiation to the output port for conveyance to the controller. The processor is configured to use the determined location of maximum detected radiation, knowledge of an excitation plan implemented by the radiating device, and an expected location of maximum radiation to determine a revised excitation plan to be implemented by the radiating device. The processor is configured to iterate the revised excitation plan to be implemented by the radiating device until the determined location of maximum detected radiation is within an acceptable distance from the expected location of maximum radiation. The processor is configured to actuate the positioning mechanism to initially move the radiation detector to at least one of: (1) a geometric central axis if the radiating device is a Gamma Knife, and (2) an expected maximum radiation location of a linear accelerator beam if the radiating device is a linear accelerator. The processor is configured to actuate the positioning mechanism to move the radiation detector based on a radiation strength previously detected by the radiation detector.

In general, in another aspect, the invention provides a computer-implemented method of using a radiating device, the method including using at least one processor to apply radiation from the radiating device in accordance with a first excitation plan, actuate a positioning mechanism to move a radiation detector, configured to receive radiation and to provide radiation strength indicia of amounts of radiation received, in three dimensions within a volume to provide information regarding radiation strength in the volume from the radiating device, analyze the radiation strength indicia from the radiation detector, correlate positions of the radiation detector with corresponding amounts of received radiation, determine a first location of maximum detected radiation, determine a first relationship between the first location of maximum detected radiation and a second location of maximum radiation, and determine a second excitation plan based upon the first relationship.

Implementations of the invention may include one or more of the following features. The method further includes using the at least one processor to iterate the second excitation plan until the first relationship satisfies at least one desired criterion. The at least one desired criterion includes that the first relationship indicates a positional variance between the first location and the second location that is less than a threshold variance. The second location of maximum radiation is one of (1) an expected location of maximum radiation and (2) a determined location of maximum radiation detected under a second radiation condition that is different than a first radiation condition in effect when the radiation was detected leading to the determination of the first location. The second radiation condition is a different angle of application of radiation by the radiating device, with the radiating device being a linear accelerator.

Implementations of the invention may include one or more of the following features. The method further includes using the at least one processor to determine a first magnitude of maximum detected radiation, and determine a second relationship between the first magnitude of maximum detected radiation and a second magnitude of maximum radiation. The second magnitude of maximum radiation is one of (1) an expected magnitude of maximum radiation and (2) a determined magnitude of maximum radiation detected under a second radiation condition that is different than a first radiation condition in effect when the radiation was detected leading to the determination of the first location. The second radiation condition is a different angle of application of radiation by the radiating device, with the radiating device being a linear accelerator.

In general, in another aspect, the invention provides a radiation field detection system for use with a radiating device, the detection system including a radiation detector configured to receive radiation and to provide radiation strength indicia of amounts of radiation received, a positioning mechanism connected to the radiation detector and configured to physically move the radiation detector, a processor coupled to the positioning mechanism and coupled to the radiation detector to receive the radiation strength indicia, the processor being configured to: actuate the positioning mechanism to move the radiation detector to a desired location within a radiation field produced by the radiating device; actuate the positioning mechanism to alter an orientation of the radiation detector relative to the radiating device while at the desired location; analyze the radiation strength indicia from the radiation detector while in different orientations relative to the radiating device while at the desired location; and determine a desired orientation of the radiation detector for the desired location such that artifacts are reduced.

Implementations of the invention may include one or more of the following features. The processor is further configured to correlate positions of the radiation detector with corresponding radiation amounts, and determine a location of the radiation detector corresponding to a highest amount of detected radiation. The processor is configured to actuate the positioning mechanism to initially orient the radiation detector to have a central axis of a radiation beam from the radiating device be substantially perpendicular to a stem of the radiation detector. The processor is configured to determine the desired position such that alteration of the orientation of the radiation detector in any direction results in a decrease in detected radiation.

Embodiments of the invention have been used to determine or map a multi-dimensional beam strength versus position to produce a beam profile of a radiation beam in a radiating device such as a Gamma Knife. Based on this beam profile, embodiments of the invention have been used to discover that the three dimensional volume of space that the intersection of radiation beams produces in a Gamma Knife may not be shaped or formed precisely or exactly as expected. Instead, there may be slight deviations, by as much as one or two percentage points of relative beam strength in certain areas of the beam profile of a Gamma Knife.

Various aspects of the invention may provide one or more of the following capabilities. A three-dimensional radiation profile of a radiation field produced by a radiating device may be measured. Radiation profiles of high dose-gradient radiation distributions can be accurately measured. The resolution, and thus rate, of measurements may be adjusted depending upon the gradient of the radiation field. Changes in the location of the maximum radiation strength for a particular device over time due to various effects, e.g., temperature changes, tolerance deviations and/or mechanical wear of the radiating device, different configurations of devices (e.g., different leaf configurations), etc. may be measured and determined and compensations for such changes implemented. Nature and strength characteristics can be determined for a radiation distribution of a radiating device, including its shape and strength at different locations or positions in three dimensions within a multiple beam intersection area (as with the Gamma Knife) or across a cross sectional area of one or more beams. Information can be determined that can be used to conform treatment of a patient to account for variations in beam strength relative to expected beam strengths. Quasi real-time feedback of a measured radiation beam profile (i.e., strength at different positions in three dimensions) of one or more radiation beams can be provided and used to adjust dosimetry for a subsequent treatment using the one or more radiation beams. Also, real-time feedback of measured radiation (i.e., strength at fixed position in three dimensions) of one or more radiation beams can be provided and used to adjust dosimetry for a current treatment, during which the radiation is measured, using the one or more radiation beams. Beam profiles may be measured, analyzed, and/or provided to devices for processing in real-time. A radiation detector can move into, across, around in, and out of a radiation field in multiple dimensions and directions and at varying speeds. The shape and/or strength of a radiation beam and/or distribution that a radiating device produces can be determined in three dimensions. Determinations can be made of off-axis deviation of beam strength, e.g., along the z-axis of a Gamma Knife such that the radiation field profile produced by the intersecting Gamma radiation beams is slightly elongated and thus somewhat stronger (e.g., two percent stronger at 1 millimeter from the isocenter of the Gamma Knife) along the Z-axis. Strength and position of off-axis deviation and can be used to conform patient treatment to account for this deviation. More accurate treatments may be provided to patients with less radiation of non-targeted tissue than with prior techniques. Radiation treatment can be more accurately prescribed and the sum total of tolerance deviations and other mechanical influences that can affect beam profile can be accounted for and/or compensated.

These and other capabilities of the invention, along with the invention itself, will be more fully understood after a review of the following figures, detailed description, and claims.

DETAILED DESCRIPTION OF PREFERRED EMBODIMENTS

Embodiments of the invention provide mechanisms and techniques for determining a three-dimensional radiation profile of a radiation field produced by a radiating device (e.g., a radiosurgery device, Gamma Knife, linac, IMRT, IMPT, etc.). In operation of embodiments of the invention, an operator places a radiation detector within a radiation field produced by the radiating device. The radiation detector is connected to a positioning device, such as a three-stage or three-dimensional micrometer system that allows for positioning of the radiation detector within the radiation field along three dimensions. As the operator incrementally or continuously positions (i.e., moves) the radiation detector within the radiation field, a controller device collects both radiation strength values, as provided by the radiation detector, along with corresponding radiation detector location values (i.e., positions), as provided by the positioning device. The controller maps the radiation strength values and location values to a three-dimensional coordinate system to produce a three-dimensional radiation profile (i.e., a beam profile) of the radiation field. Using the radiation profile, the operator can determine the strength of the radiation field at any location that is a within the three-dimensional coordinate system, including the location of the maximum detected radiation strength of the radiation field.

Embodiments of the invention can also detect and measure deviations from an expected radiation field that a radiating device produces. The radiating device experiences some unexpected aspect of its operation, such as patient table axis wobble, wearing of ball bearings or other rotation mechanisms that position a gantry on a linac thus producing some amount of gantry sag due to gravity or patient misspositioning due to table axis wobble. Embodiments of the invention can detect changes to the beam profile due to such factors and can account for such variances in a treatment plan for the patient.

Figure 1:
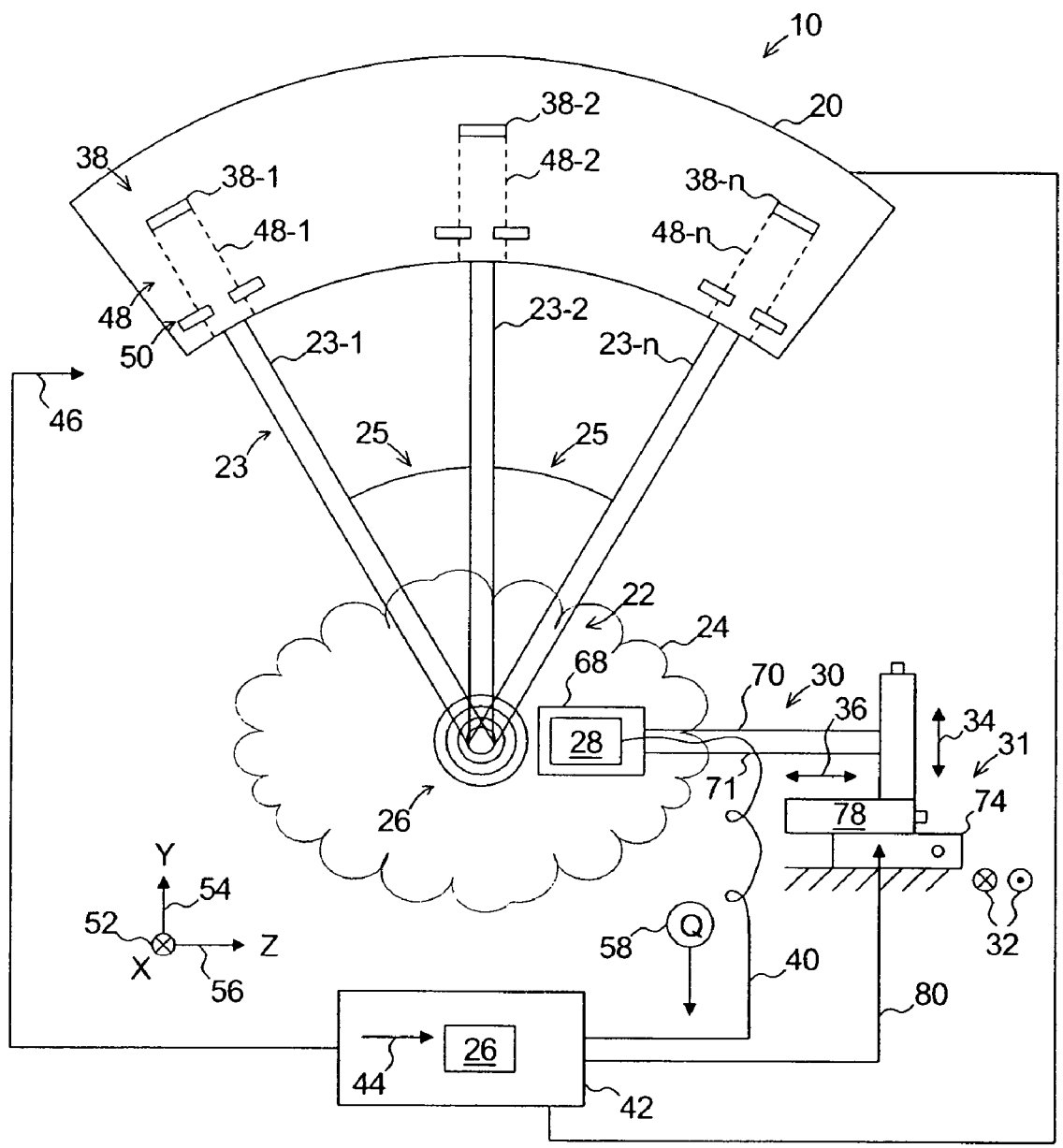
FIG. 1 shows a block diagram of a radiation profile detection system.

FIG. 1 illustrates an exemplary radiation profile detection system 10. The radiation profile detection system 10 includes a radiating device 20, a radiation detector 28, a positioning device 30 coupled to the radiation detector 28, and a system controller 42.

The radiating device 20 produces or directs a radiation field 22 to a spatial volume 24. The spatial volume 24 is defined as a three-dimensional space, such as defined in the x-axis 52, y-axis 54, and z-axis 56 of the Cartesian coordinate system. The radiating device 20 has a radiation source 38, a collimator portion 48, and a shield portion 50. The radiation source 38 produces ionizing radiation such as gamma radiation and the collimator portion 48 acts to collimate or narrow the radiation emitted by the radiation source 38 into a relatively narrow beam. The shield portion 50 may be moveable, e.g., if the radiating device 20 is a linac, relative to the collimator portion 48. The shield portion 50 is formed of a relatively dense material (e.g., lead, or tungsten) that, when configured in a closed position relative to the collimator portion 48, prevents or limits the radiation produced by the radiation source 38 from exiting the collimator portion 48 toward undesired portions of the spatial volume 24, e.g., healthy tissue.

The radiating device 20 produces multiple radiation beams 23 at multiple angles 25 relative to the spatial volume 24 to create the radiation field 22. For example, the radiating device 20 may be a Gamma Knife having multiple radiation sources 38-1, 38-2, 38-N and collimator portions 48-1, 48-2, 48-N positioned at various locations within the radiating device 20, to produce multiple radiation beams 23-1, 23-2, 23-N at respective angles relative to the spatial volume 24. In another example, the radiating device 20 is a linear accelerator having a radiation source 38, collimator portion 48, and shield portion 50 that moves or rotates relative to the spatial volume 24, thereby allowing for the production of multiple radiation beams 23-1, 23-2, 23-N at multiple angles 25 relative to the spatial volume 24.

The radiation detector 28 measures the strength (e.g., fluence or intensity) of the radiation field 22 produced by the radiating device 20. When exposed to the radiation field 22 the detector 28 produces a current 58 in real-time where the amount of current 58 produced by the radiation detector 28 is proportional to the strength of the radiation field 22 at a given location within the spatial volume 24. The volume of the radiation detector 28 is relatively smaller than the detection volume of conventional radiation detectors (e.g., conventional ion chambers having a 0.6 $cm^3$ or 0.2 $cm^3$ volume). For example, the radiation detector 28 may be a silicone diode detector having a 0.06 mm thick by 0.6 mm diameter active dimension with 0.017 $mm^3$ detection volume. Alternatively, the radiation detector 28 may be a diamond detector having a 0.5 mm thick by 4 mm diameter active dimension. Such relatively small radiation detectors 28 provide relatively higher spatial resolution than do conventional ion chambers with respect to the radiation field 22.

A phantom 68 encompasses the radiation detector 28 during the radiation profile detection process. The phantom 68 simulates the effect of soft tissue when exposed to a radiation field 22 and creates a scatter effect with respect to the radiation field 22 produced by the radiating device 20. The phantom 68 may be formed of a polystyrene material or water encased in a plastic shell.

The positioning device 30 allows for three-dimensional positioning of the radiation detector 28 within the spatial volume 24 relative to the radiating device 20. For example, the positioning device 30 is formed of three connected, mutually perpendicular micrometer devices 74, 76, 78 (e.g., micrometers coupled to single axis moveable stages). The first micrometer 74 provides x-direction motion 32, the second micrometer 76 provides y-direction motion 34, and the third micrometer 78 provides z-direction motion 36 of the radiation detector 28 relative to the spatial volume 24. Each micrometer 74, 76, 78 has a resolution of 0.01 mm, thereby allowing for sub-millimeter positioning of the radiation detector 28 within the spatial volume 24.

The radiation detector 28 couples to an arm 70 of the positioning device 30. The arm 70 includes a length 71 between the radiation detector 28 and a base 31 of the positioning device 30. The arm length 71 allows placement of the base 31 of the positioning device 30 outside of the radiation field 22 produced by the radiating device 20 while allowing exposure of the radiation detector 28 within the radiation field 22 during radiation profile detection. In the case where an operator (e.g., a medical physicist) manually adjusts the positioning device 30 to change the location of the detector 28 within the radiation field 22, the length 71 of the arm 70 helps to minimize the operator's exposure to the radiation field 22 where the radiating device 20 is a Gamma Knife.

The controller 42 is a computerized device, such as a data collection device, that collects, stores, and processes the charge and/or current values 58 produced by the radiation detector 28 when exposed to the radiation field 22. The controller 42 is configured with calibration data to convert the charge values 58 into radiation strength values in real-time (at the speed of a processor of the controller 42). The controller 42, furthermore, collects corresponding three dimensional location information of the radiation detector 28 within the spatial volume 24 as provided by the positioning device 30. As shown, the controller 42 receives indicia of the charge 58 produced by the radiation detector 28 through a connector 40, such as a wire. The controller 42 may communicate with the radiating device 20 to control the application of the radiation field 22 to the spatial volume 24. This feedback may affect application of the radiation in real-time, during patient treatment, or in quasi-real-time between treatments. For example, the controller 42 causes the radiation shield portion 50 to move from a blocking position (e.g., preventing radiation from traveling from the radiation source 38 to the spatial volume 24) to an open position to allow radiation to travel from the source 38 to the spatial volume 24.

The controller 42 can communicate with the positioning device 30 to provide automatic motion control of the positioning device 30 relative to the spatial volume 24. For example, the controller 42 forms a feedback loop 80 between the radiation detector 28 and the positioning device 30. The feedback loop 80 allows the controller 42 to actuate the positioning device 30 based upon the amount of current 58 produced by the radiation detector 28 (indicating the strength of the radiation field 22 at any point within the spatial volume 24). The operator can use the detector 28 to search for a maximum radiation strength or dose location (i.e., "hot spot") within the spatial volume 24. As the detector 28 moves through the radiation field 22 within the spatial volume 24, the detector 28 transmits charge values 58 to the controller 42 where each charge value 58 indicates the strength of the radiation field 22 at a given location within the spatial volume 24. The controller 42 iteratively compares charge values 58 received from the radiation device 28 and uses the values 58 to continually actuate the positioning device 30 along all three axes 52, 54, 56 within the spatial volume 24. The controller 42 determines the absolute maximum current value (i.e., maximum radiation strength or "hot spot") within the spatial volume 24 in real-time (e.g., as opposed to waiting to develop film disposed in the radiation field 22). Preferably, the controller 42 determines the hot spot as the information regarding radiation strength becomes available from the detector 28.

As described above, by positioning the detector 28 along three dimensions within the spatial volume 24, the controller 42 determines the relative strength of the radiation field 22 within the spatial volume 24. The controller 42 collects charge values 58 from the radiation detector 28, produced by exposure of the radiation detector 28 to the radiation field 22, along with corresponding detector 28 location information or values provided by the positioning device 30, within the spatial volume 24. The controller 42 uses the charge values 58 (e.g., radiation strength values) and the corresponding location information to determine a radiation profile 26 (e.g., the three-dimensional radiation profile) of the radiation field 22 in real-time (e.g., by correlating the data as they are received or otherwise become available). Therefore, the radiation profile 26 of the radiation field 22 relates the strength of the radiation field 22 to each three dimensional location within the spatial volume 24 to which the radiation field 22 is applied.

The speed at which the detector 28 is moved through the field 22 may be varied. The controller 42 may determine the dose gradient of the present location of the detector 28 and slow the detector's speed to increase the accuracy of measurement in high dose-gradient regions and increase the detector's speed in low dose-gradient regions to accelerate the process of data acquisition. The increased speed can save cost associated with determining the profile.

Figure 2:
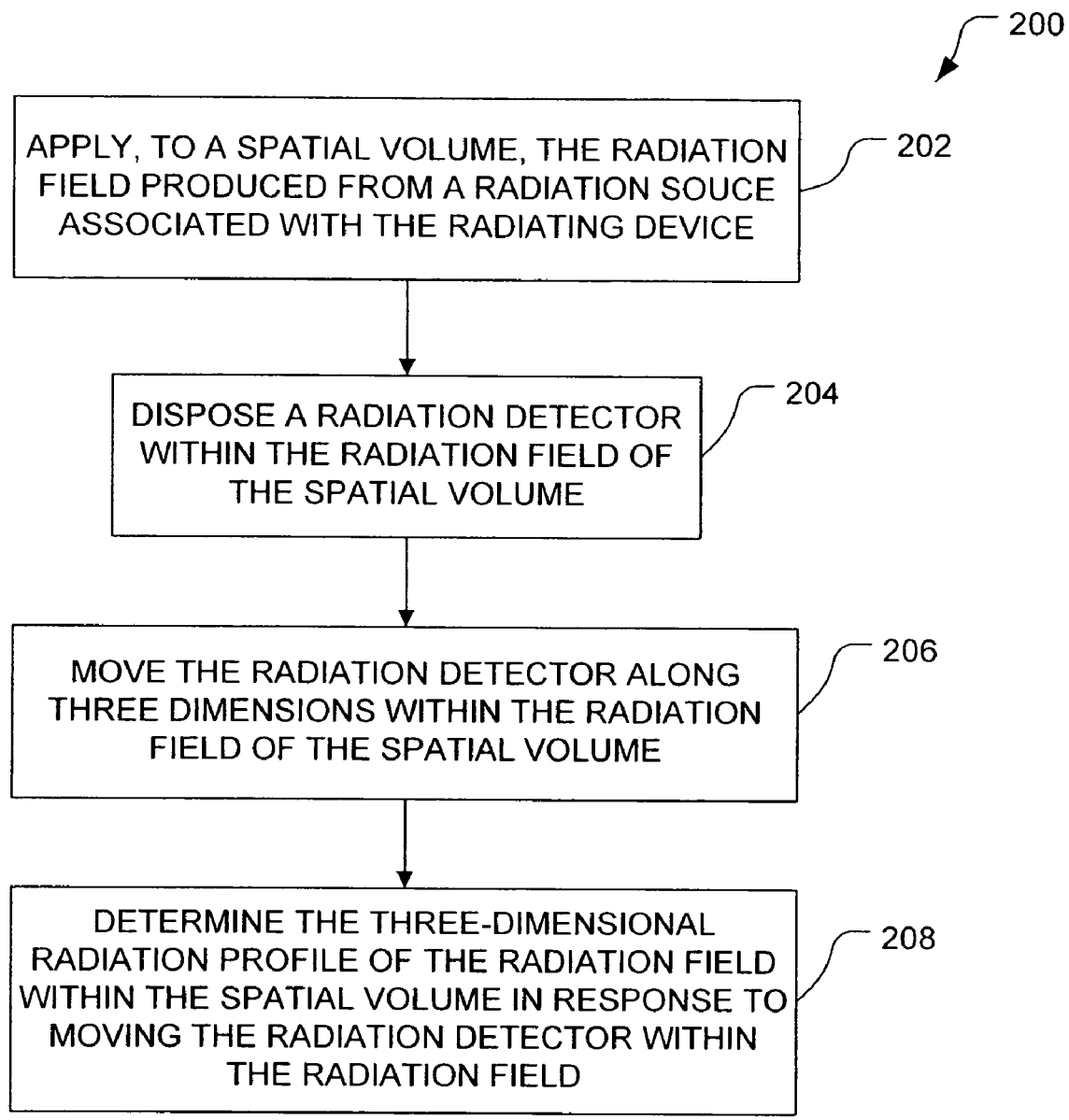
FIG. 2 illustrates a flowchart showing a method of determining a radiation profile performed using the system of FIG. 1.

FIG. 2 illustrates a flowchart showing a method 200 performed by the controller 42, according to embodiments of the invention. The method 200 is exemplary and not limiting. In the method 200, the controller 42 determines the three-dimensional radiation profile 26 of the radiation field 22 produced by the radiating device 20.

In stage 202, the controller 42 causes the radiating device 20 to apply, to the spatial volume 24, the radiation field 22 produced from the radiation source 38 associated with the radiating device 20. For example, the controller 42 actuates the radiation shield portion 50 such that the shield 50 moves from a closed position to an open position, thereby allowing radiation from the radiation source 38 to travel through the collimator portion 48 and form the radiation field 22 within the spatial volume 24. As described, the radiation field 22 is an ionizing radiation field created by gamma radiation, for example. The radiation field 22 provides a radiation dose to a particular region of interest within a specimen.

In stage 204, the radiation detector 28 is disposed within the radiation field 22 of the spatial volume 24. For example, as described with respect to FIG. 1, the radiation detector 28 is coupled to the positioning device 30 that provides for three-dimensional positioning of the radiation detector 28 within the spatial volume 24. The controller 42 communicates with the positioning device 30 to automatically position the radiation detector 28 and/or the device 30 is manually actuated to position the detector 28 (e.g., by the operator manipulating the controller 42) within the spatial volume 24 (e.g., in proximity to or in the radiation field 22 generated by the radiating device 20). For example, by utilizing the above-described feedback loop (e.g., through iterative positioning and measuring), the controller 42 continuously moves the radiation detector 28 within the spatial volume 24 until the controller 42 determines or receives a charge 58 from the radiation detector 28. Initial reception of such a charge 58 indicates to the controller 42 that the detector 28 is entering (at an edge of) the radiation field 22.

Referring to FIG. 1, if the radiation detector 28 moves along the z-axis of the spatial volume 24, as the radiation detector 28 moves through the radiation field 22, interaction between the radiation field 22 and the radiation detector 28 causes the detector 28 to emit a charge 58. For locations within the spatial volume 24 where the radiation detector 28 does not intersect the radiation field 22, the radiation detector 28 does not produce a charge 58. As the radiation detector 28 enters the radiation field 22 and approaches a "hot spot" location, the charge 58 produced by the radiation detector 28 increases.

In stage 206, the controller 42 moves the radiation detector 28 three dimensions within the radiation field 22 of the spatial volume 24. For example, as described, the controller 42 is in communication with the positioning device 30 and causes the positioning device 30 to move the radiation detector 28 within the radiation field of the spatial volume 24. The controller 42 moves or positions the radiation detector 28 and phantom 68 within the radiation field 22 along all three axes 52, 54, 56 that define the spatial volume 24. Here, the controller 42 actuates each micrometer 74, 76, 78 to create three-dimensional motion of the radiation detector 28 within the radiation field 22. As each micrometer 74, 76, 78 of the positioning device 30 has a positioning resolution of 0.01 mm, the controller 42 can extremely accurately position the detector 28 within the spatial volume 24.

In stage 208, the controller 42 determines 26 the three-dimensional radiation profile 26 of the radiation field 22 within the spatial volume 24 in response to moving the radiation detector 28 within the radiation field 22. The three-dimensional radiation profile 26 indicates a strength of the radiation field 22 at sampled locations within the spatial volume 24. The controller 42 incrementally positions the radiation detector 28 within the radiation field 22 in the spatial volume 24 to determine the radiation profile 26 of the radiation field 22. The radiation field 22 within the spatial volume 24 has a varying strength (e.g., fluence or intensity) with respect to the spatial volume 24. The three-dimensional radiation profile 26, therefore, relates the strength of the radiation field 22 with a particular location within the spatial volume 24. In conjunction with stage 206, the controller 42 increase the speed of the detector's motion in low dose-gradient regions and reduces the speed of the detector's motion in high dose-gradient regions.

As described above, the radiation detector 28 produces a charge 58 when exposed to a radiation field 22 where the charge value 58 is proportional to the strength of the radiation field 22. As the radiation detector 28 produces the charge 58 while moving through the radiation field 22, the controller 42 collects the charge values 58 along with the corresponding location values of the radiation detector 28 within the spatial volume 24. For example, the controller 42 collects the location values or location information from the positioning device 30 at each location within the spatial volume 24 relating to a particular charge value 58. By correlating or mapping the charge values 58, indicating radiation field strength, with the respective location values of the radiation detector 28, within the spatial volume 24, the controller 42 determines a three-dimensional radiation profile 26 of the radiation field 22.

The three-dimensional radiation profile 26 allows an operator to determine the strength of the radiation field 22 at any point within the spatial volume 24. For example, the radiation profile 26 allows an operator to determine a location, relative to the spatial volume 24 that receives the maximum radiation strength (e.g. radiation dose) produced by the radiating device 20 in the volume 24. There may be more than one point at which a maximum radiation level is detected. The amounts may be identical in actuality and/or may be within a tolerance/accuracy, e.g., 1%, of the radiation detector 28. Values that are not identical but within the detector's accuracy may be treated as being equal. Multiple maxima may be adjacent to each other and/or spaced apart from each other. Further, the radiation profile 26 may be analyzed to determine surfaces of equal radiation levels. The radiation profile 26 also allows the user to determine an "edge" of the radiation field 22 (e.g., locations within the volume 24 that receive minimal amounts of radiation from the radiating device 20 when the volume 24 is exposed to the radiation field 22), the volumetric shape of the radiation field 22 (e.g., whether the radiation field 22 produced by the radiation source 38 has a spherical shape or an ovular shape), and the orientation of the volumetric shape of the radiation field 22 with respect to the spatial volume 24 (e.g., non-symmetric orientation about one axis, such as the z-axis, relative to the spatial volume).

As illustrated in FIG. 1, the controller 42 conforms 46 a radiation treatment of a specimen (e.g., a patient), subject to the radiation field 22, based upon the determined radiation profile 26. For example, during a radiosurgery treatment, an operator exposes a region of interest within a patient, such as an intracranial lesion, to the radiation field 22 produced by the radiating device 20. Prior to the radiation treatment, the radiation oncologist creates a surgical strategy to position or move the patient within the radiation field 22 such that the intracranial lesion intersects the location of maximum radiation strength or dose produced by the radiating device 20. The oncologist also tailors the surgical strategy to try to minimize the amount of radiation that tissue surrounding the lesion receives. In the case where the radiation profile 26 indicates a nonsymmetric (e.g., rotated) radiation field 22 relative to the spatial volume 24, the operator can adjust the radiation application based upon the nonsymmetric radiation field 22 by either adjusting the location of the intracranial lesion relative to the radiation field 22 and/or the oncologist can change the dose strategy by changing dose strength or radiation strength produced by the radiation field 22, for example. In such a case, by using the radiation profile 26, the radiation profile 26 can be used to limit/reduce inadvertent or unnecessary overexposure of tissue surrounding the lesion to radiation produced by the radiating device 20.

Conformance of the radiation strategy and/or application can be done in real-time during treatment of a patient or in quasi-real-time between treatments. For example, during treatment, the detector 28 may be inserted into the patient in vivo, e.g., in a cavity in the patient. The field 22 at that point can be monitored by the controller 42 and indicia of the field at that point provided to the device(s) controlling the positioning of the patient and/or the application of the radiation. For example, if the expected field at the detector is known, the delivery parameters of the radiation may be adjusted if the strength at the detector 28 is not what is should be, e.g., to adjust the magnitude and/or location of the actual maximum radiation. The detector 28 could be moved to provide three-dimensional information to help determine appropriate adjustments for applying the radiation. Further, or alternatively, the magnitude of all or part of the radiation field may be increased if the detected strength is below an expected value, and decreased if the detected radiation is above an expected value. These adjustments can be made during the radiation of the patient. Alternatively, adjustments to how the radiation is applied (e.g., positioning of the patient and/or delivery parameters for the radiating device 20) may be adjusted between treatments of the patient. In this case, the system 10 is preferably used to determine the three-dimensional profile 26 of the radiation. Using this information, the physicist and/or oncologist may make appropriate adjustments.

As described above, the radiation detector 28 produces a charge 58 when exposed to a radiation field 22 produced by the radiating device 20. In certain cases, the radiation beam profile (e.g., the cross-sectional shape of the beam(s)) is relatively narrow compared to the size of the detector 28. Therefore, as the radiation detector 28 is exposed to the relatively narrow beam 23, the beam 23 intersects or activates only a portion of the detector 28. The charge value 58 that represents such exposure, as produced by the detector 28, however, is based upon the average charge produced by the entire volume of the detector 28 when exposed to the narrow beam. Therefore, in the case where the radiation detector 28 is substantially larger than the profile of the beam, the output charge value 58 from a radiation detector 28 can be substantially lower than the actual strength of the beam 23. Such a phenomenon is known as volume averaging in radiation detectors 28. Volume averaging by radiation detectors 28 can lead to inaccuracies when determining the strength of the radiation field 22 within the spatial volume 24.

The system 10 allows for correction of volume averaging effects of the radiation detector 28 by utilizing off-axis ratio measurements with respect to the radiation field 22. The off-axis ratio relates to the ratio of a strength of the radiation field 22 at an off-axis location relative to a maximum strength (e.g., maximum dose) within the radiation field 22. Using the off-axis ratio for a radiation field 22, the effect of volume averaging by the radiation detector 28 can be reduced to help correct the radiation strength values (e.g. charge values 58) produced by the radiation detector 28. The off-axis ratio for the radiation field 22 of a radiating device 20 can be determined using radiation sensitive (e.g., radiographic or radiochromic) film.

Figure 3:
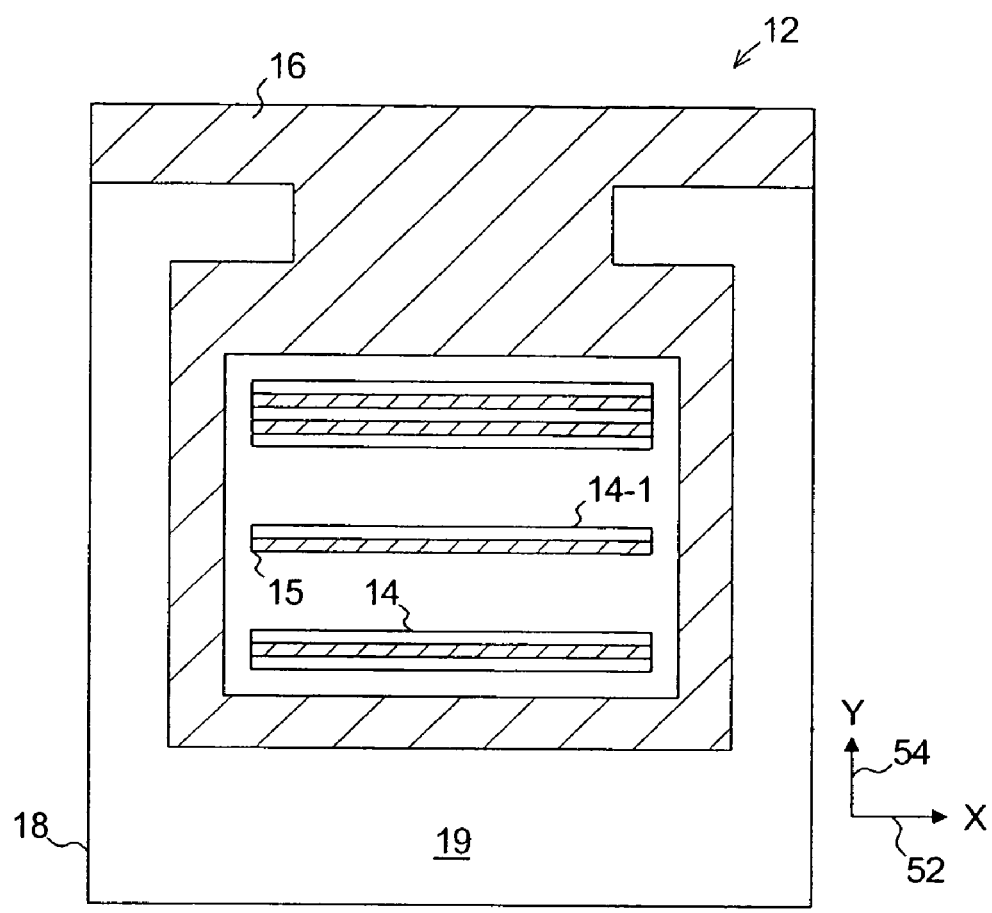
FIG. 3 illustrates a phantom used for optical density measurements.

FIG. 3 illustrates an off-axis ratio detector 12. The detector 12 includes a film housing 16 that holds alternating layers of radiation sensitive film 14 and spacing material 15. The film housing 16 fits in a phantom 18 containing a water gel material 19.

The film housing 16 is formed of a polystyrene material and houses, e.g., 18, pieces or layers of radiation sensitive film, such as a Kodak X-Omat V film, each having a thickness of 0.2 mm and a diameter of 14 mm. The spacing material 15 is a silver-free film substrate spacer. The spacers 15 absorb Auger electrons emitted in the radiation field 22 that can contaminate otherwise abutting film elements 14. The water gel material 19 of the detector 12 creates a scatter effect of the radiation field 22 produced by the radiating device 20. Such a scatter effect mimics the scatter effect on the radiation field as produced by soft tissue exposed to a similar radiation field 22.

To determine the off-axis ratio with respect to a radiation field 22, the off-axis ratio detector 12 is positioned within a radiation field 22, thereby allowing for exposure of the films 14 within the radiation detector 12 to the radiation field 22. After film irradiation, the films 14 are removed from the film housing 16 and the optical density of each film layer 14 is measured. For example, an optical densitometer can be used to measure the net optical density distribution of the film. Next, calibration curves are used to correlate net optical density and strength, and the net optical distribution measurements are converted to a dose or strength of the radiation field 22. The off-axis ratio is calculated for a location on the film 14 by relating the radiation strength at that location with the maximum strength value of the film 14. In this manner, off-axis ratio values can be determined over the two-dimensional surface of the film 14.

Figure 4:
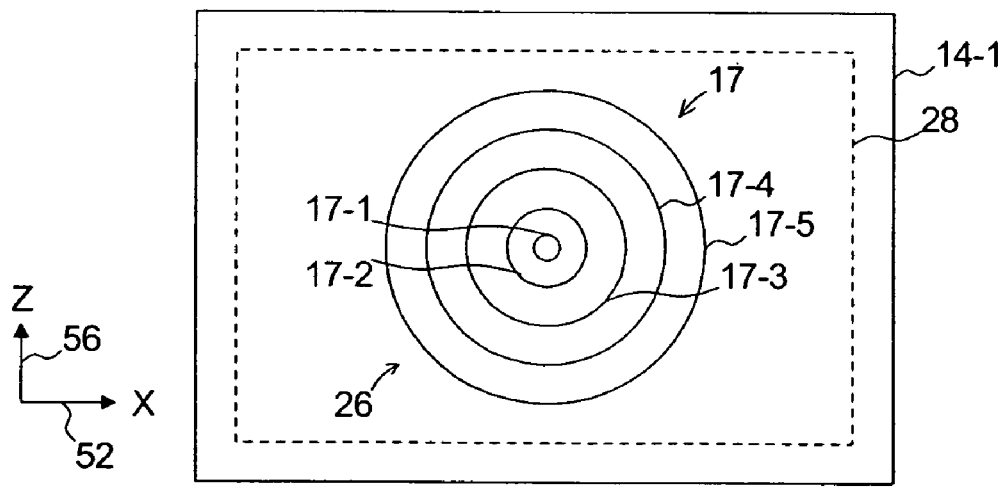
FIG. 4 illustrates a block diagram of a film from an optical density measurement.

FIG. 4 illustrates an irradiated film element 14-1 from the off-axis ratio detector 12, shown in FIG. 3. For illustrative purposes, and by way of example only, the film 14-1 shows a two-dimensional radiation profile 26 as a series of concentric circles 17. Circle 17-1 indicates a location within the radiation profile 26 having the maximum radiation strength. With increasing diameter (e.g., relatively larger concentric circles 17) of the radiation profile 26, the film 14-1 indicates a decreasing dose or radiation strength of the radiation field 22 produced by the radiating device 20. Therefore, because the radiation strength decreases with increasing diameter, the off-axis ratio of the radiation profile 26 decreases with increasing radiation profile diameter.

Figure 5:
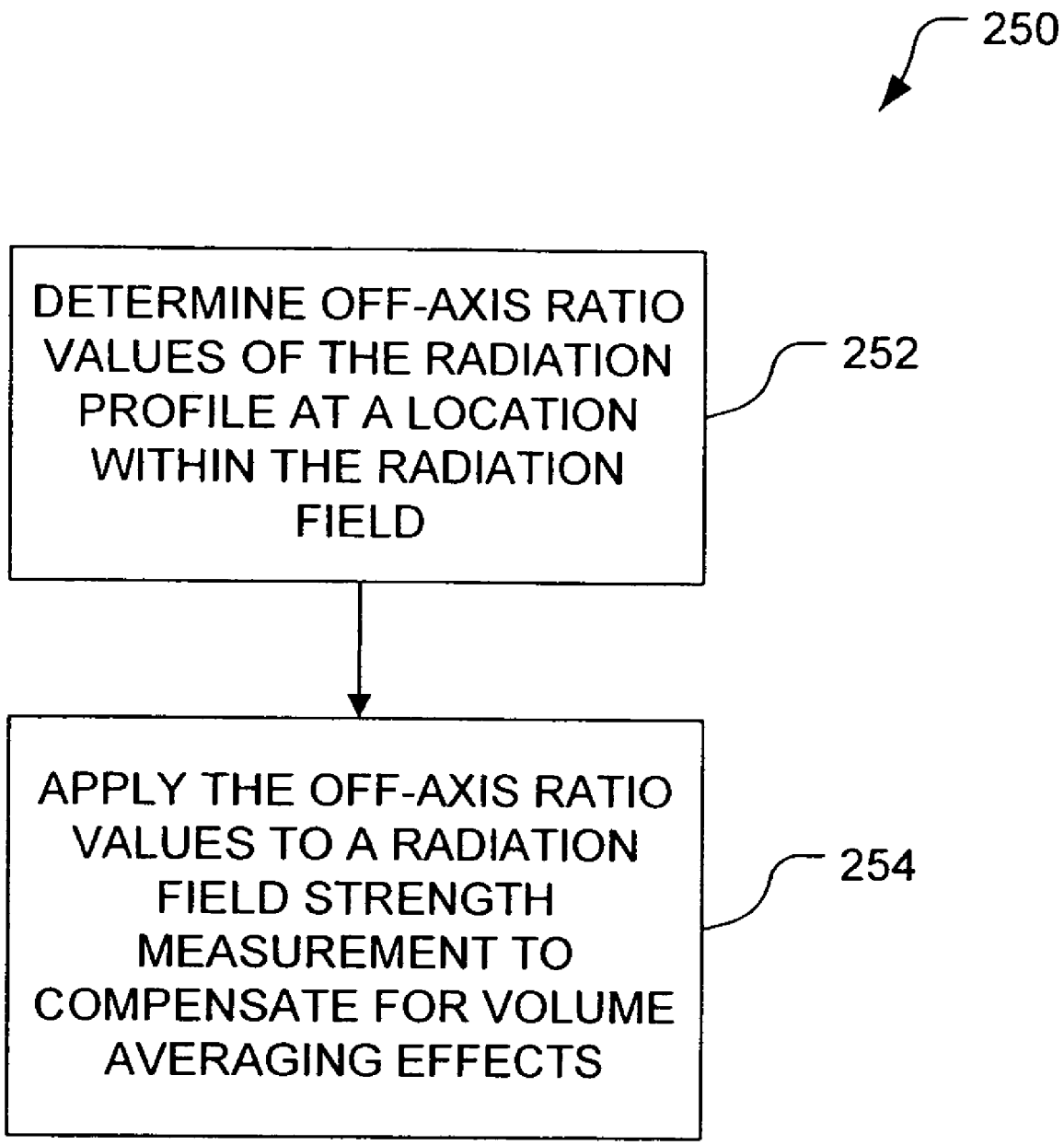
FIG. 5 illustrates a flowchart showing a method of compensating for volume averaging effects.

FIG. 5 illustrates a flowchart showing a method 250 performed by the controller 42, according to embodiments of the invention. The method 250 is exemplary and not limiting. The method 250 allows for correcting volume averaging effects of the radiation detector 28 utilizing the determined off-axis ratios for a radiation field 22.

In stage 252, the controller 42 determines the off-axis ratio value of the radiation profile 26 at a given location within the radiation field 22. For example, assume that concentric ring 17-1 represents the location of maximum radiation strength in the radiation profile 26. The controller 42 then determines off-axis ratios between the radiation strengths of each concentric ring 17-2, 17-3, 17-4, 17-5 and the radiation strength at the maximum strength location, ring 17-1.

In stage 254, the controller 42 applies the off-axis ratio values to a radiation field strength measurement, determined at the given location, to correct for volume averaging effects produced by the radiation detector 28. For example, assume a radiation detector 28 measures a radiation strength value, within a spatial volume 24, at a location corresponding to the location of the radiation detector 28 shown in FIG. 4. As shown, the radiation detector 28 intersects locations of varying radiation strength, represented by concentric rings 17-1, 17-2, 17-3, 17-4, and 17-5. In the case where the radiation beam has a narrow profile, relative to the size of the detector 28, volume averaging by the radiation detector 28 produces a relatively lower radiation strength value than the strength of the beam itself. The controller 42 applies the off-axis ratios for each ring 17-1, 17-2, 17-3, 17-4, and 17-5 to the radiation strength measurement produced by the radiation detector 28, at the illustrated detector 28 location, to compensate for the volume averaging effects of the detector 28. The controller 42 may perform such an application by integrating the off-axis ratios over the volume of the detector, such as described in "Small-beam Calibration by 0.6- and 0.2-cm$^3$ Ionization Chambers," *Med. Phys.* 11(6) 1984, incorporated herein by reference.

After determining the radiation profile 26 of a radiation field 22 created by the radiating device 20, the controller 42 utilizes the radiation profile 26 to determine variances or changes among multiple radiation profiles 26 acquired over time, for a single radiating device 20, for example. By comparing various radiation profiles 26 for a single radiating device 20, discrepancies or changes in the radiating device 20 over time can be detected and corrections in treatment can be made to compensate for the detected changes in the radiating device 20.

Figure 6:
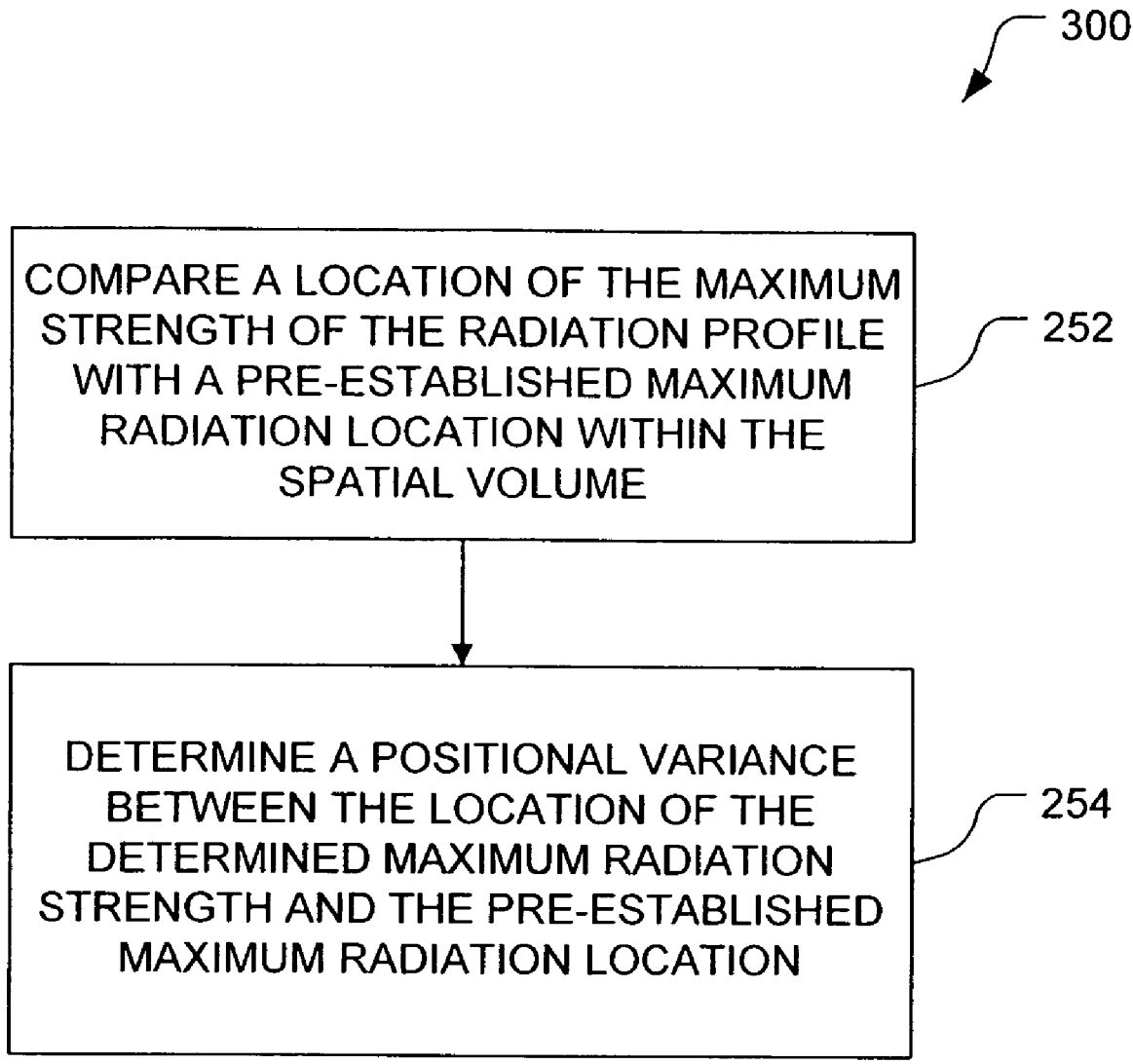
FIG. 6 illustrates a flowchart showing a method of determining a positional variance.

FIG. 6 illustrates a flowchart showing another method 300 performed by the controller 42, according to embodiments of the invention. The method 300 is exemplary and not limiting. The method 300 provides information relating to physical changes in the radiating device 20 over time.

In stage 302, the controller 42 compares a location of the determined maximum radiation strength of the radiation profile 26 of the radiation field 22 with a predicted location of the maximum radiation strength within the spatial volume 24. Conventionally, radiating device manufacturers provide an expected location of the maximum radiation strength of the radiating device 20 (e.g., a pre-established radiation profile). For example, in the case where the radiating device 20 is a Gamma Knife, the location of the pre-established maximum radiation strength corresponds to the mechanical or geometric center of a helmet associated with the Gamma Knife. The actual location of maximum strength may deviate from the geometric center, e.g., because the beams of the Gamma Knife are not symmetric about the geometric center. Thus, path lengths to one side of the geometric center are longer with corresponding increased attenuation, so that the maximum strength is on the side of the geometric center closer to the beam sources. For a linac, the expected location of maximum strength is typically given as the geometric center but the actual location may deviate from this, e.g., due to transmission through the collimating leaves, imperfect positioning of the leaves, radiation leakage between the leaves, and/or gantry sag. Using the above-described techniques, the actual location of maximum radiation strength in a radiation field 22 produced by the radiating device 20 can be found.

For example, the controller 42 determines the radiation profile 26 of the radiation field 22 by mapping radiation strength values and corresponding location values, with respect to a spatial volume 24, to a three-dimensional coordinate system, as described above. Using the radiation profile 26, the controller 42 determines the location of the determined maximum radiation strength (e.g. maximum dose strength) of the radiation field 22. The controller 42 compares the location of the determined maximum radiation strength with the location of the pre-established maximum radiation strength, as provided by the manufacturer of the radiating device 20.

In stage 304, in response to the stage of comparing, the controller 42 determines a positional variance between the location of the determined maximum radiation strength and the pre-established maximum radiation location. Thus, a difference in the determined location of the maximum radiation strength of the radiation field 22, e.g., along any axis 52, 54, 56 with respect to the spatial volume 24, with respect to the location of the maximum radiation strength of the radiation field 22 as provided by the manufacturer is determined to be a positional variance.

In response to determining the positional variance between the location of the detected maximum radiation location and the pre-established maximum radiation location, the controller conforms 46 a radiation treatment of a specimen, subject to the radiation field 22, to account for the determined positional variance. For example, assume that the controller 42 determines a difference, such as a 2 mm difference along the z-axis 56, between the location of the maximum radiation strength of the radiation field 22, as detected by the radiation detector 28, and a location of the maximum radiation strength of the radiation field 22 as pre-established by the manufacturer. During treatment, the controller 42 can adjust the positioning of the specimen within the radiation field 22 along the z-axis to account for the 2 mm difference. Such positioning exposes the specimen (e.g., a location of interest within the specimen, such as an intracranial lesion) to the correct maximum radiation location (e.g., the determined maximum location) rather than the pre-established maximum radiation location. The positioning allows for application of the maximum radiation strength to the appropriate location (e.g., tumor or lesion) within a patient.

The method 300 shown in FIG. 6 can help with calibration of the medical devices 20 and determination of physical changes to the medical devices 20 over time. The method 300 is applicable to various types of radiating devices 20. For example, the method 300 can be applied to radiating devices 20 having a stationary radiation source 38 and that allow for positioning of a specimen relative to the radiation field 22, such as in a Gamma Knife. Alternatively, the method 300 can be applied to radiating devices 20 having a radiation source 38 that moves relative to a stationary specimen, such as in a linear accelerator.

Figure 7:
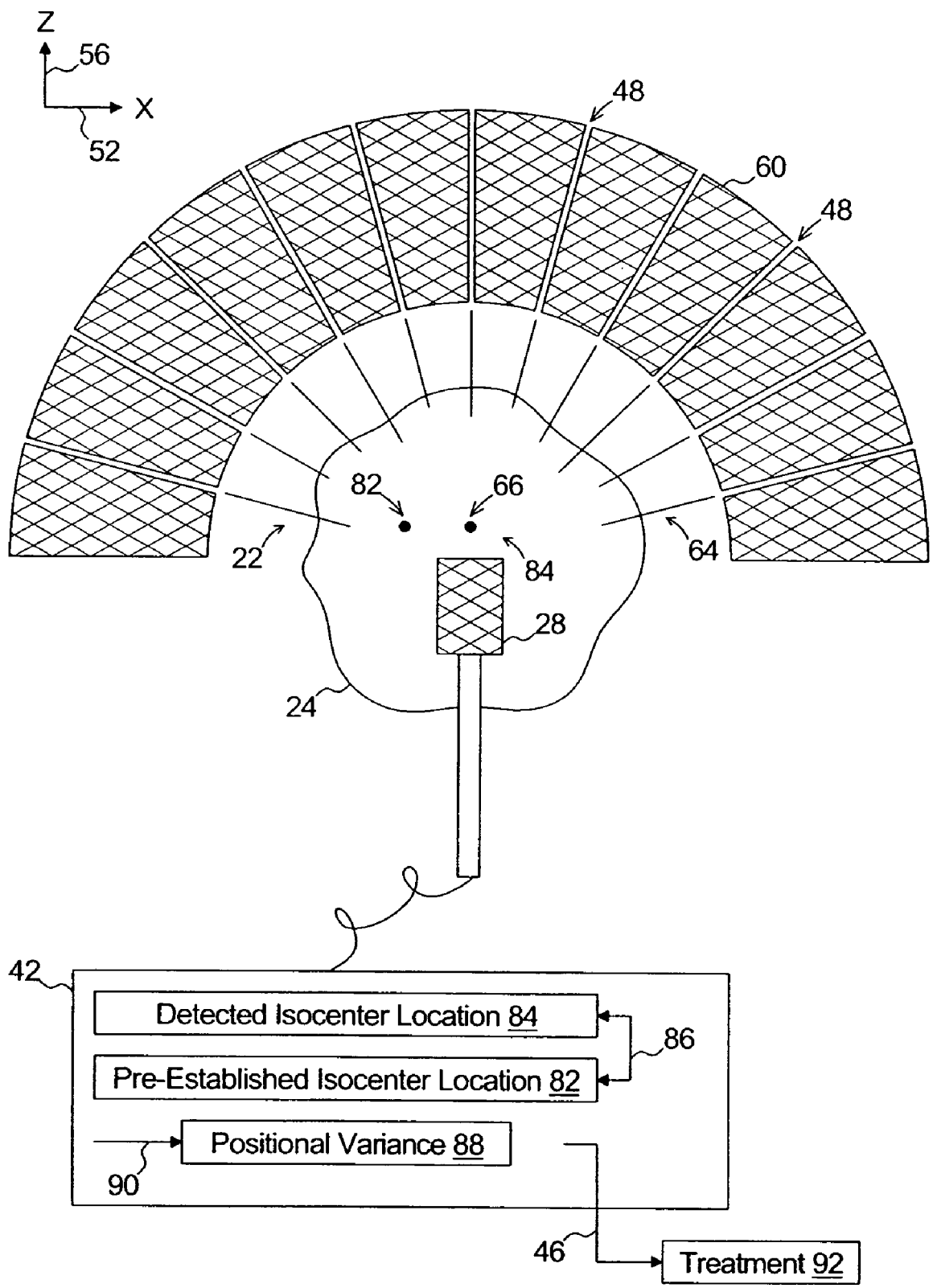
FIG. 7 illustrates, along top view, a block diagram of a Gamma Knife.

FIG. 7 illustrates the radiating device 20 as a Gamma Knife 60 (Leskell Gamma Knife, Elekta Instruments, Atlanta, Ga.). The Gamma Knife contains 201 cobalt-60 sources (e.g., gamma radiation sources) and 201 corresponding separate, removable collimators 48. Each collimator 48 acts to shape radiation emitted from a corresponding radiation source 38 into a radiation beam 64. During operation, the Gamma Knife 60 produces an overlap of all 201 radiation beams 64 from the collimators 48 at an isocenter location 66 or a location of maximum radiation strength of the radiation field 22.

The Gamma Knife 60 can be configured with like-sized collimators 48 such that the Gamma Knife 60 includes a series of either 4 mm diameter, 8 mm diameter, 14 mm diameter, or 18 mm diameter collimators 48. Each diameter collimator 48 creates a different beam profile of the radiation from the radiation source 38. The smaller the diameter of the collimator 48, the narrower the profile of the radiation beam 64 emitted from the Gamma Knife 60. The size of the beam profile of the radiation beam affects the diameter of radiation field 22 at the isocenter location 66. For example, 4 mm collimators 48 produce a radiation field 22 having a smaller diameter than the radiation field produced by the 18 mm collimators 48.

Theoretically, the isocenter 66 of the Gamma Knife is equivalent to a pre-established maximum radiation strength (e.g., isocenter) location, as provided by the manufacturer. Using the above-described apparatus and methods, a controller 42 or a person (e.g., a qualified medical physicist) can determine a correspondence between the pre-established isocenter and a measured or detected isocenter location. This provides a "check" regarding the accuracy of the pre-established isocenter location regardless of the beam profile produced by the various sized collimators 48.

Figure 8:
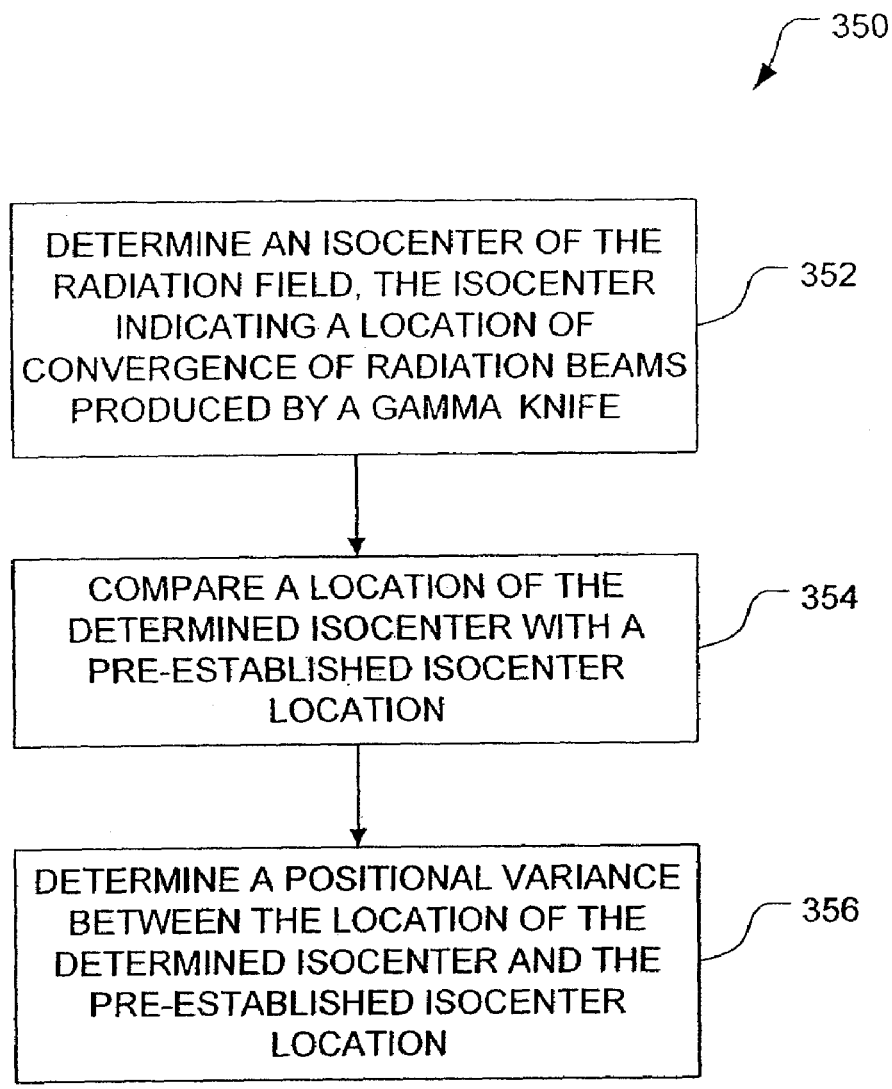
FIG. 8 illustrates a flowchart showing a method of determining a positional variance.

FIG. 8, taken in conjunction with FIG. 7, illustrates a flowchart showing a method 350 performed by the controller 42. The method 350 is exemplary and not limiting. In the method 350, the controller 42 determines the accuracy of the pre-established isocenter location of the radiation field 22 produced by the Gamma Knife 20.

In stage 352, the controller 42 determines an isocenter 84 of the radiation field 22. The isocenter 84 indicates a location of convergence of a plurality of radiation beams 64 produced by the Gamma Knife 60. The controller 42 receives, from the radiation detector 28, radiation field strength values (e.g., charge values 58) and, from the positioning device 30, location values (e.g., coordinates relative to the spatial volume 24) corresponding to the detected strength values. The controller 42 determines the isocenter location 84 of the Gamma Knife, for example, by iteratively comparing successively collected radiation field strength values to determine the maximum radiation strength value for the radiation field 22. The controller 42, in turn, determines the coordinates or location, relative to the spatial volume 24, that correspond to the maximum radiation strength value. For example, assume that the determined isocenter 84 of the Gamma Knife has coordinates of (x, y, z).

In stage 354, the controller 42 compares 86 a location of the determined isocenter 84 of the radiation field 22 with a pre-established isocenter location 82 within the spatial volume 24. The controller 42 is configured with (e.g., stores within a memory location) the pre-established isocenter location 82 of the Gamma Knife 60. When performing the stage of comparing, the controller 42 performs a mathematical computation with respect to the coordinates of the pre-established isocenter location 82 and the determined isocenter location 84. For example, assume that the pre-established isocenter 82 of the Gamma Knife has coordinates of (x−1, y, z). During the comparison process, the controller 42 subtracts the coordinates (x−1, y, z) of the pre-established isocenter 82 from the coordinates (x, y, z) of the determined isocenter 84.

In stage 356, the controller 42 determines 90, in response to the stage of comparing 86, a positional variance 88 between the location of the determined isocenter 84 and the pre-established isocenter location 82. Using the above example, subtracting the pre-established coordinates (x−1, y, z) from the determined coordinates (x, y, z) produces a resulting difference between the coordinates of (1, 0, 0). The results of the comparison 86 indicate that the location of the pre-established isocenter 82 is, located along the x-axis 52, one unit away from the determined isocenter location 84. Because the results of the comparison 86 do not show a direct correspondence between the pre-established isocenter 82 and the determined isocenter location 84 (e.g., overlapping isocenters), the controller 42 determines the positional variance 88 between the isocenter locations 82, 84.

Based upon the determined positional variance 88, the controller 42 conforms a radiation treatment of a specimen, subject to the radiation field 22, to account for the positional variance 88 between the location of the determined isocenter 84 and the pre-established isocenter location 82. For example, as described above, the controller 42 adjusts the positioning of the specimen within the radiation field 22 to account for the determined offset between the isocenter locations 82, 84, thereby exposing the specimen to the correct maximum radiation location (e.g., the determined maximum location).

Figure 9:
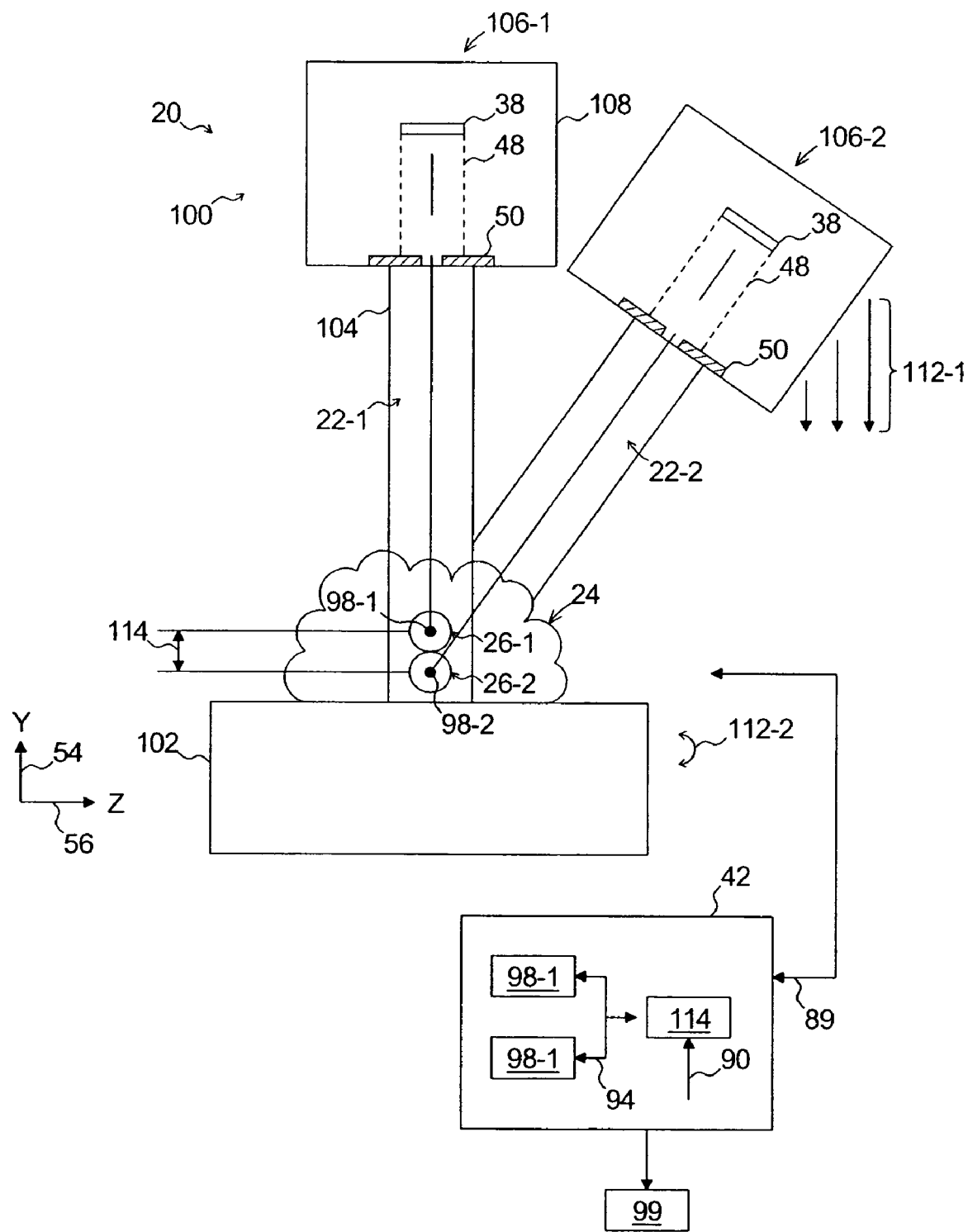
FIG. 9 illustrates a block diagram of a linear accelerator.

FIG. 9 illustrates the radiating device 20 as a linear accelerator 100. The linear accelerator 100 includes a gantry head 108 having a radiating source 38 and a single collimator 48 including a radiation shield 50 formed of multiple leaves. The multi-leaf collimator 48 produces radiation fields 22 of varying shapes, depending upon the placement of the leaves 50 of the collimator 48 relative to the radiation source 38. The linear accelerator 100 further includes a specimen stage 102 and a gantry arm 104 coupled to a gantry head 108 and rotatably positionable relative to the specimen stage 102. The specimen stage 102 allows placement of a specimen within the radiation field 22 delivered by the multi-leaf collimator 48 of the gantry head 108. The gantry arm 104 rotates the gantry head 108 about the specimen stage 102 and provides for the application of overlapping radiation fields 22 to a target location in the specimen. Such overlapping allows for application of an effective radiation field that conforms to the geometry of the target location of the specimen.

Theoretically, as the gantry arm 104 rotates about the stage 102, the location of a radiation profile 26 of the radiation field 22, as produced by the linear accelerator 100 and relative to the spatial volume 24, should remain constant (e.g., the position of the radiation profile relative to the spatial volume 24 remains relatively unchanged as the gantry arm 104 rotates). Using the above-described apparatus and methods, the controller 42 determines motion of the radiation profile 26 within the spatial volume 24 as the gantry arm 104 rotates relative to the stage 102. This provides a "check" regarding the accuracy of the location of the radiation profile 26 within the spatial volume 24 at various gantry arm 104 positions relative to the specimen stage 102.

Figure 10:
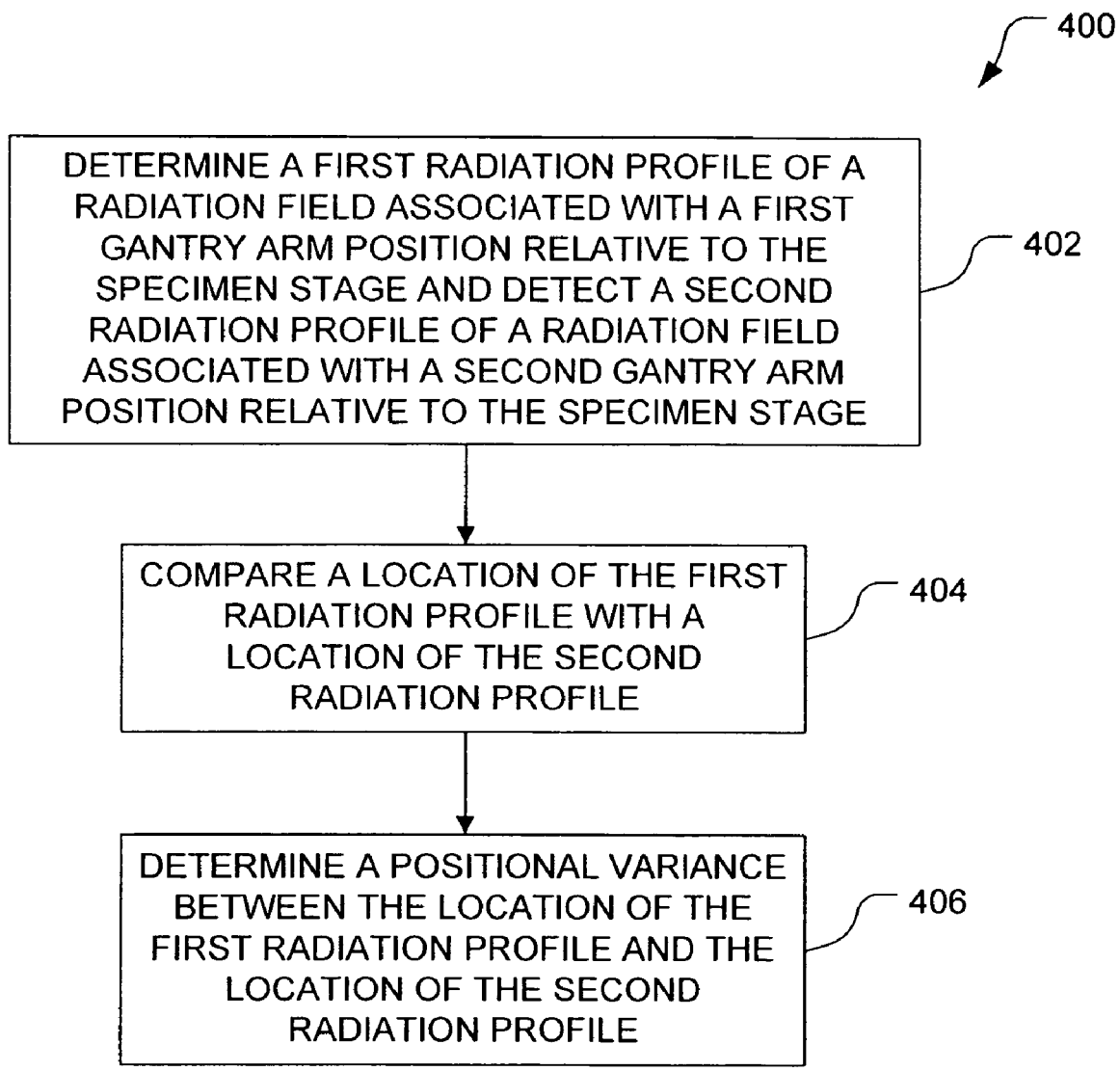
FIG. 10 illustrates a flowchart showing a method of determining a positional variance.

FIG. 10, taken in conjunction with FIG. 9, illustrates a flowchart showing a method 400 performed by the controller 42 according to embodiments of the invention. The method 400 is exemplary and not limiting. In the method 400, the controller 42 determines, relative to the spatial volume 24, the positional accuracy of each radiation profile 26 created by the linear accelerator 100 during rotation of the gantry arm 104.

In stage 402, the controller 42 determines 89 a first radiation profile 26-1 of a radiation field 22 associated with a first gantry arm position 106-1 relative to the specimen stage 102. The controller 42 also determines 89 a second radiation profile 26-2 of a radiation field 22 associated with a second gantry arm position 106-2 relative to the specimen stage 102. For example, the controller 42, as described above, utilizes the radiation detector 28 and the positioning device 30 to collect radiation field strength values (e.g., charge values) and location values (e.g., coordinates corresponding to the strength values). Based upon the radiation field strength values and the location values, the controller 42 determines (e.g., maps to a three-dimensional coordinate system) the radiation profile 26 for each gantry arm position 106-1, 106-2 of the linear accelerator relative to the specimen stage 102.

In stage 404, the controller 42 compares 94 a location 98-1 of maximum radiation strength of the first radiation profile 26-1 with a location 98-2 of the second radiation profile 26-2. For example, assume the location 98-1 of the first radiation profile 26-1 has center point coordinates of (x, y, z) and the second location 98-2 of the second radiation profile 26-2 has center-point coordinates of (x, y−1, z). When performing the comparing, the controller 42 performs a mathematical computation with respect to the coordinates of the first location 98-1 of the first radiation profile 26-1 and the second location 98-2 of the second radiation profile 26-2. During the comparison process, for example, the controller 42 subtracts the coordinates (x, y, z) of the first radiation profile 26-1 from the coordinates (x, y−1, z) of the second radiation profile 26-2.

In stage 406, the controller 42 determines 90 a positional variance 114 between the location 98-1 of the first radiation profile 26-1 and the location 98-2 of the second radiation profile 26-2. Using the above example, subtracting the first radiation profile coordinates (x, y, z) from the second radiation profile coordinates (x, y−1, z) produces a resulting difference between the profile coordinates of (0, −1, 0). The results of the comparison 86 indicate that the second location 98-2 of the second radiation profile 26-2 is, along the y-axis 54, one unit away from the first location 98-1 of the first radiation profile 26-1.

Such positional variance can have one or more of various causes. For example, the positional variance 114 determined between the first radiation profile 26-1 and the second radiation profile 26-2 may result from a positional abnormality 112 of the linear accelerator 100. The positional abnormality 112 may involve displacement of the gantry arm 104 during rotation in a phenomenon called "gantry sag" 112-1. For example, as the gantry arm 104 rotates from the first position 106-1 (e.g., the gantry arm 104 perpendicular to the stage 102) to the second position 106-2 (e.g., the gantry arm 104 forms an angle <90° relative to the stage 102), gravity generates a y-component force on the gantry head 108. The y-component force creates a bending moment (e.g., force multiplied by gantry arm length normal to the force) on the gantry arm 104 about the center of rotation of the gantry arm 104. In turn, the bending moment creates a rotational displacement or "sag" in the gantry head 108 relative to the stage 102. The gantry sag, in turn, leads to changes in the positions or locations of the radiation profiles 26-1, 26-2 created by the linear accelerator.

The positional abnormality 112 may (also) involve "table axis wobble" 112-2 of the specimen stage 102. Table axis wobble 112-2, e.g., relates to positional variances created during positioning of the stage 102 as caused by mechanical or tolerance errors in the mechanisms controlling motion of the specimen stage 102. For example, tolerance inconsistencies in the bearings used to support the stage 102 can cause positioning errors in moving the stage 102 from a first position to a second position. The positional abnormality 112 may (also) involve changes to the internal components of the of the gantry head 108, such as the bending magnets, electronics that form the radiation beam, and leafs of the multi-leaf collimator 48, as caused by gravitational forces on the components.

After determining the positional variance 114 in the radiation profiles 26-1, 26-2, as caused by positioning of the gantry arm 104, the controller 42 conforms 99 a radiation treatment of a specimen to account for the positional variance 114 between the location 98-1 of the first radiation profile 26-1 and the location 98-2 of the second radiation profile 26-2. For example, the controller 42 can adjust the positioning of the specimen within the radiation field 22 (e.g., such as by using the stage 102) to account for the determined positional variance 114, thereby exposing the specimen to the maximum radiation strength location at any gravity arm position 106.

Figure 11:
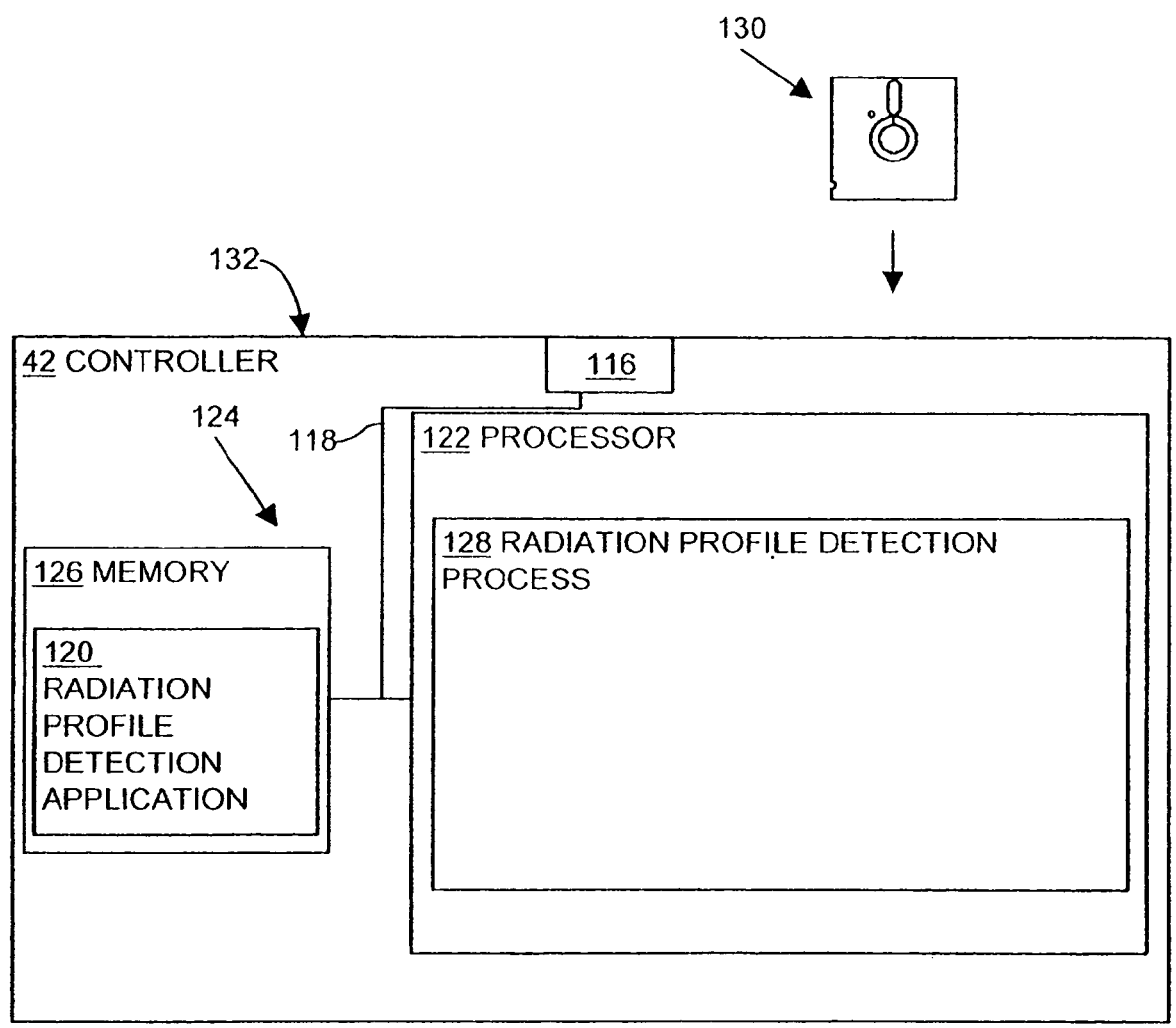
FIG. 11 is a block diagram of a computerized device.

FIG. 11 illustrates a more detailed architecture of the controller 42, configured as a computerized device 132. A computer program product 130 includes an application or logic instructions, such as radiation profile detection instructions, that are stored in the computerized device 132 to configure the controller 42 to determine a radiation profile 26 of a radiation field 22 produced by a radiating device 20.

The controller 42 includes an interconnection mechanism 118 such as a data bus and/or other circuitry that interconnects a computerized device controller 124, including a memory 126 and a processor 122, and one or more communications interfaces 116.

The memory 126 can be one or more of various types of volatile or non-volatile memory or storage such as computer memory (e.g., random access memory (RAM), read-only memory (ROM), or other electronic memory), disk memory (e.g., hard disk, floppy disk, optical disk (e.g., CDROM) and so forth). The memory 126 is encoded with logic instructions (e.g., software code) and/or data that form a radiation profile detection application 120 configured according to embodiments of the invention. In other words, the radiation profile detection application 120 represents software code, instructions and/or data that represent or convey the processing logic functions and operations as explained herein and that reside within memory or storage or within any computer readable medium accessible to the controller 42.

The processor 122 represents one or more of various types of circuitry or processing devices such as a central processing unit, microprocessor or application-specific integrated circuit that can access the radiation profile detection application 120 encoded within the memory 126 over the interconnection mechanism 111 in order to execute, run, interpret, operate or otherwise perform the radiation profile detection application 120 logic instructions. Doing so forms the radiation profile detection process 128. In other words, the radiation profile detection process 128 represents one or more portions of the logic instructions of the radiation profile detection application 120 while being executed or otherwise performed on, by, or in the processor 122 within the controller 42.

Another example of operation of an embodiment of the invention illustrates some capabilities of the aforementioned embodiments. For this example, consider a patient table 102 that operates in conjunction with a linear accelerator gantry (e.g. gantry arm 104 and gantry head 108) in order to provide oncology treatment to the patient while the patient is lying on the table 102 during treatment with a radiation beam 23. The treatment may involve using a radiation beam 23 produced from the gantry head 108 mounted on the gantry arm 104 that rotates in multiple dimensions around (e.g., relative to) the patient table. In addition, the patient table 102 can be rotated on its horizontal axis (e.g., in a circle) to provide optimal positioning for the patient such that the beam of radiation 23 from the linear accelerator 100 can contact a target region of the patient's body in a precise location. Various existing software programs produce treatment regimes or plans which govern how to precisely control patient table rotation and linear accelerator gantry rotation as well as radiation beam strength and exposure time in order to optimally expose the affected area of a patient at a precise angle for treatment by a radiation beam 23 of a prescribed strength or dose.

Utilizing embodiments of the invention, a qualified person, e.g., a qualified medical physicist, can periodically (e.g., daily or weekly or just prior to patient treatment) place embodiments of the invention including the three-dimensional positioning device 30 and attached radiation detector 28 on the patient table 102 such that the radiation detector 28 is positioned at the current isocenter of the radiation beam 23 produced by the linear accelerator 100. Thereafter, during constant application of the radiation beam 23 to the radiation detector 28 of this invention, the physicist can activate rotation of the gantry arm 104 of the linear accelerator 100 and/or of the patient table while continuously monitoring relative strength of the beam 23 profiled using the radiation detector 28. Since embodiments of the invention are able to detect and provide real-time feedback as to the relative strength of the radiation beam 23 at any particular position associated with the detector 28, a feedback loop 80 can be provided to the positioning mechanism 30 such that the positioning mechanism 30 can continuously reposition, if needed, the radiation detector 28 to precisely track any movement of the isocenter or "hot-spot" of the radiation beam 23 during table rotation or during gantry arm rotation of the linear accelerator 100. In other words, embodiments of the invention can be used to track, in real-time, the actual movement of the isocenter of a linear accelerator radiation beam in order to profile (e.g., create a radiation profile for) this beam and its associated movement when moving the gantry or table to and from various positions.

Accordingly, since the positioning mechanism 30 can be configured to cause the radiation detector 28 to continuously, in real-time, track the strongest portion of the radiation beam 23, if the gantry arm 103 of the linear accelerator 100 suffers from gantry sag due to gravitational or other mechanical abnormalities or faults, or if the patient table 102 experiences table axis wobble 112-2 during its rotation, or if any other component introduces slight deviations into the beam profile, embodiments of the invention are able to track these deviations and are thus able to produce a map or model of the radiation profile 26 while accounting for such positioning or other errors.

Patient table axis wobble 112-2, gantry sag 112-1, and/or other mechanical influences that affect the shape of the beam profile or its position can be accounted for and/or compensated. Accordingly, when a patient is positioned on the table 102 during application of radiation during a treatment regime, software or other computerized processing that computes beam strength application to a patient at various positions of the linear accelerator gantry head 108 and patient table 102 accounts for the effects of gantry sag and table axis wobble or other mechanical influences as detected and modeled by embodiments of the invention. The treatment regime can be conformed according to the determined beam profile while under the effects of mechanical influences such as gantry sag, table axis wobble or other such factors.

Other embodiments are within the scope of the invention.

Figure 12:
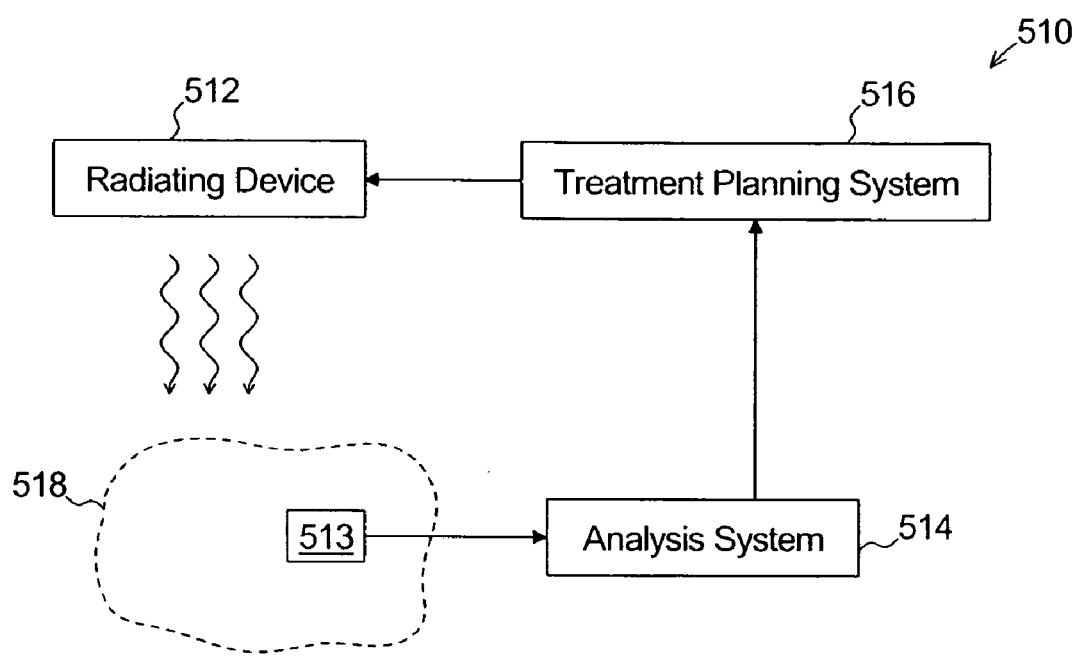
FIG. 12 is a block diagram of a radiation detection system that provides feedback of actual radiation distribution.

Referring to FIG. 12, a radiation system 510 includes a radiating device 512, a radiation detector 513, a profile or dose distribution analysis system 514, and a treatment planning system 516. The radiating device may be any of a variety of devices such as a Gamma Knife or a linear accelerator (linac). The radiating device 512 is configured to radiate portions of a volume 518 (that may be a phantom or a patient, or portions thereof) and the analysis system 514 (e.g., including a controller and a positioning device similar to those described above) is configured to detect and analyze the radiation provided by the device 512.

In particular, the analysis system 514 is configured to provide feedback to the radiation controller 516 regarding the actual radiation distribution provided by the radiating device 512. For example, the system 514 can determine the location and magnitude (as indicated by current or charge detected) of actual maximum radiation. The system 514 may also determine correlations/relationships between the expected location and magnitude of maximum radiation and the actual location and magnitude of maximum radiation, respectively. The detector 513 may be positioned in a patient, e.g., in a body cavity and can be scanned through the cavity, e.g., in accordance with techniques described in U.S. Pat. No. 4,753,248. This information may be provided by the analysis system 514 to the radiation controller 516.

The controller 516 is configured to use the feedback provided by the analysis system 514 regarding actual maximum radiation location and/or magnitude to adjust delivery parameters of the radiating device. The adjustments may be made in real-time, e.g., for patient treatment, or in quasi-real-time, e.g., for quality assurance purposes. The controller 516 can determine delivery parameters and provide the expected location and magnitude of maximum radiation.

Using the feedback from the analysis system 514 (e.g., raw values of actual max radiation location and or magnitude, variance values, etc.), the controller 516 can determine revised delivery parameters and corresponding revised expected location and/or magnitude of maximum radiation (as well as the rest of the expected distribution). The radiation controller 516 can continue to iterate the delivery parameters until at least one desired criterion is met such as that the locations of the actual and expected maximum radiation are within a threshold distance of each other. Another criterion may be that magnitudes of the actual and expected maximum radiation are within a threshold strength value of each other. Another criterion may be that the actual radiation distribution, possibly regardless of conformance to expectations, provides a desired level of radiation to a desired location. Various combinations of criteria may be used, including thresholds that are dependent upon other criteria (e.g., the magnitude variance may increase as the location variance decreases).

Other embodiments providing feedback are possible. For example, the analysis system 514 (e.g., a controller of the system 514) may perform the calculation of new delivery parameters and perform the evaluation to determine when to stop iterating the plan. Further, a device other than either the radiation controller 516 or the analysis system 514 could perform these operations. This device could receive the feedback information from the analysis system 514, process the information, and provide delivery parameters to the radiation controller 516 or other data from which the radiation controller could determine excitation values for the radiating device 512.

Figure 13:
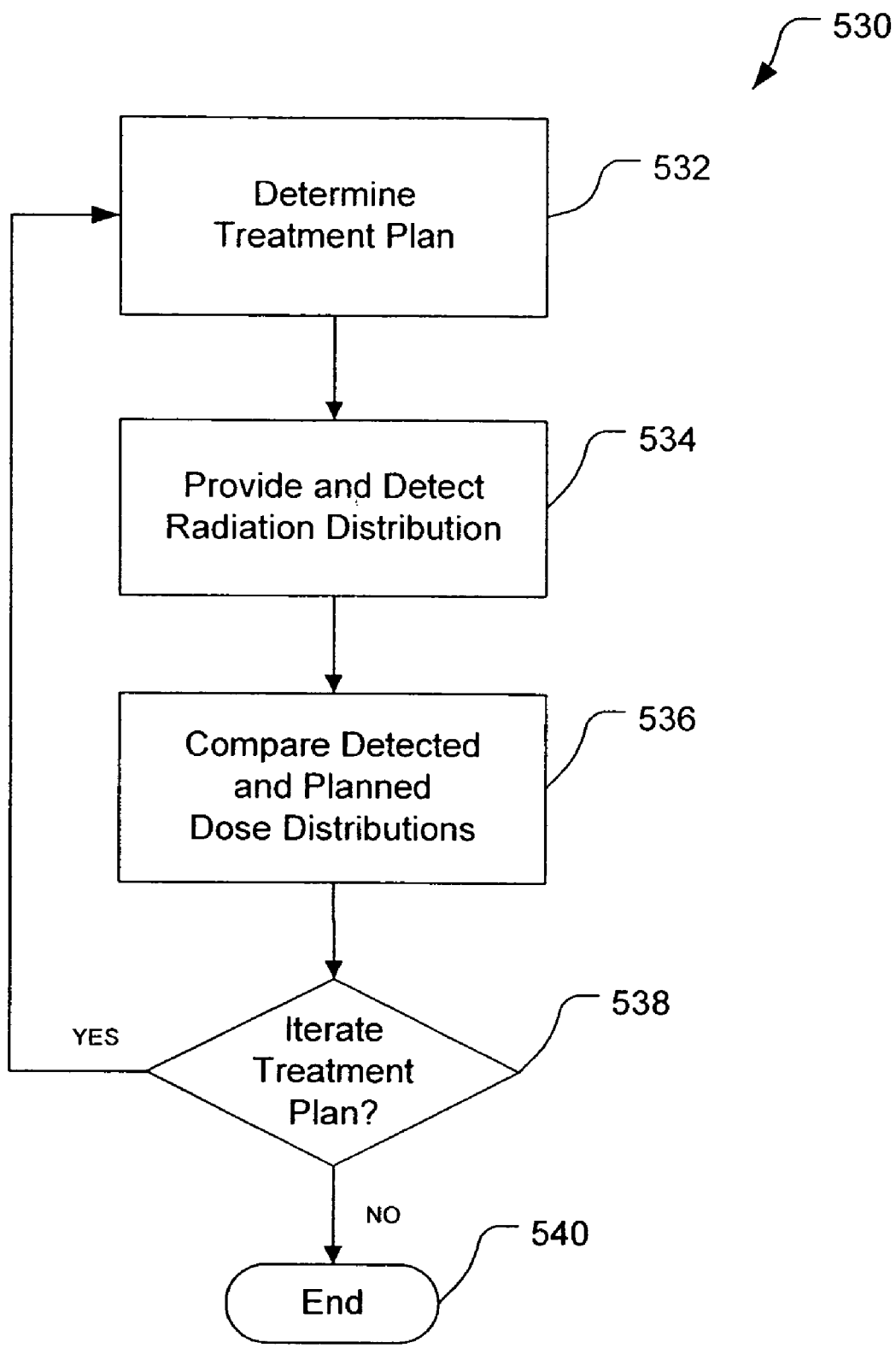
FIG. 13 is a block flow diagram of a process of using the system shown in FIG. 12 to iterate radiation distributions.

In operation, referring to FIG. 13, with further reference to FIG. 12, a process 530 for determining desired delivery parameters using the system 510 includes the stages shown. The process 530, however, is exemplary only and not limiting. The process 530 may be altered, e.g., by having stages added, removed, or rearranged.

At stage 532, the radiation oncologist uses the treatment planning system 516 to determine/develop a treatment plan. Based on desired characteristics of the radiation, the treatment planning system 516 determines how to configure the radiating device 512 and determines expected radiation distribution values.

At stage 534, the radiating device 512 provides radiation and the analysis system 514 analyzes the indicia of the detected radiation. The radiating device 512 is actuated according to the current treatment plan. The analysis system 514 determines the point of maximum radiation dose in each segment of the treatment plan by manipulating its detector 513 in three dimensions (and possibly orientation as discussed below).

At stage 536, the detected radiation is analyzed to determine actual radiation distribution values. The system 514 analyzes the detected radiation to determine values related to the actual radiation distribution and supplies these values to the appropriate device, in this example the treatment planning system 516.

At stage 538, the treatment planning system 516 uses the actual radiation distribution values from the analysis system 514 to determine if the delivery parameters need to be iterated/adjusted. If desired criteria are (or a desired criterion is) met, then the process ends at stage 540. Otherwise, the process 530 returns to stage 532 where the treatment plan is iterated/adjusted in view of the actual distribution values to try to make the actual radiation distribution meet the desired criteria (or desired criterion).

Figure 14:
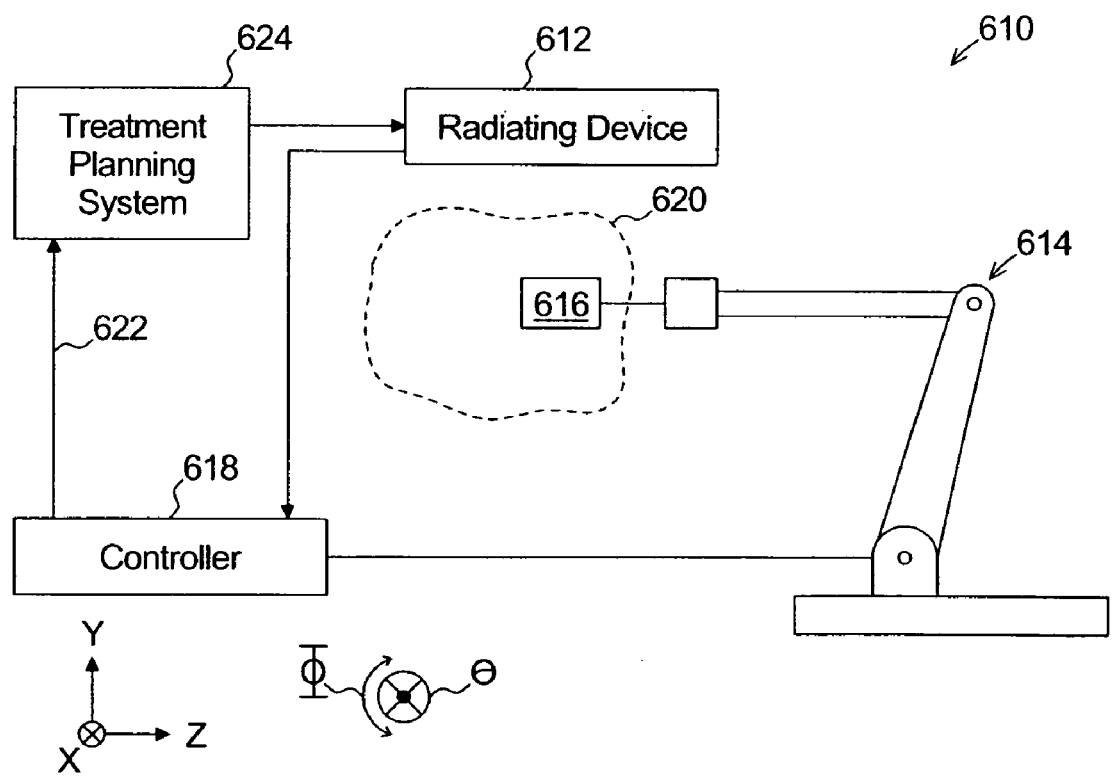
FIG. 14 is a simplified diagram of a radiation detection system for selecting a position and orientation of a radiation detector.

Referring to FIG. 14, a radiation system 610 includes a radiating device 612, a positioning mechanism 614, a radiation detector 616, a controller 618, and a treatment planning system 624. The system 610 can perform operations similar to those discussed above regarding, e.g., positioning the detector 616, determining a location of maximum radiation in a volume 620, correlating expected location and actual location of maximum detected radiation, providing information regarding the actual location of maximum detected radiation and adjusting delivery parameters of the radiating device 612. In the system 610, as opposed to the system 10 shown in FIG. 1, the positioning mechanism 614 is a micro-manipulating robotic arm.

The robotic arm 614 provides for flexibility in orientation of the radiation detector 616 within the volume 620. The robotic arm 614 is shown schematically and includes appropriate motors connected to the controller 618 for positioning and orienting the radiation detector 616 as desired. The positioner 614 can move the detector 616 in the x-, y-, and z-directions either one direction at a time or in multiple directions simultaneously, and can adjust the orientation of the detector relative to the radiating device 612. In particular, the positioner 614 can adjust the angular orientation of the detector 616 so that the detector 616 can be positioned so that its length is out of the y-z plane and/or in an orientation other than parallel to the z-axis. In other words, the detector 616 can be disposed at various angles in various planes parallel to the x-axis. Said still another way, the detector 616 can be rotated in $\Phi$ about a line parallel to the x-axis and/or in $\Theta$ about a line parallel to the y-axis as shown.

The controller 618 is configured to regulate the position and the orientation of the radiation detector 616. The controller 618 can actuate the positioning mechanism 614 with appropriate signals to cause the mechanism 614 to move the detector 616 (in particular a reference point associated with the detector 616, e.g., its mass center) to a desired location in x, y, and z coordinates within the volume 620. The controller 620 is further configured to cause the orientation of the detector 616 to be varied for the same location of the detector 616 (i.e., the same location of the detector's reference point). The position and orientation can be varied independently of each other, or simultaneously. During these variations, the detector's center may not be stationary, but may move and be returned with the detector 616 in a different orientation.

Further, the controller 618 can analyze the information provided by the detector 616 to determine the optimal orientation(s) for the detector 616 at which detector artifacts are minimized. For a standard cylindrical ion chamber radiation detector, this will typically occur when the central axis of the beam from the radiating device 612 is perpendicular to a stem that is coaxial with the charged central pin of the chamber. For a 201-beam Gamma Knife radiating device, the ideal position for such a chamber may be such that the stem is perpendicular to the central axes of equatorial beams collectively irradiating transverse anatomic planes. The controller 618 uses the detected radiation amount with the detector 616 in the optimal orientation when comparing detected radiation values of different locations in the volume 620, e.g., to determine the location and/or magnitude of the maximum detected radiation in the volume 620. The controller 618 preferably determines the point where movement of the detector 616 in any direction ($\pm$x, $\pm$y, $\pm$z) would yield a decrease in detected radiation strength, and uses this as the location of maximum radiation in the volume 620.

Figure 15:
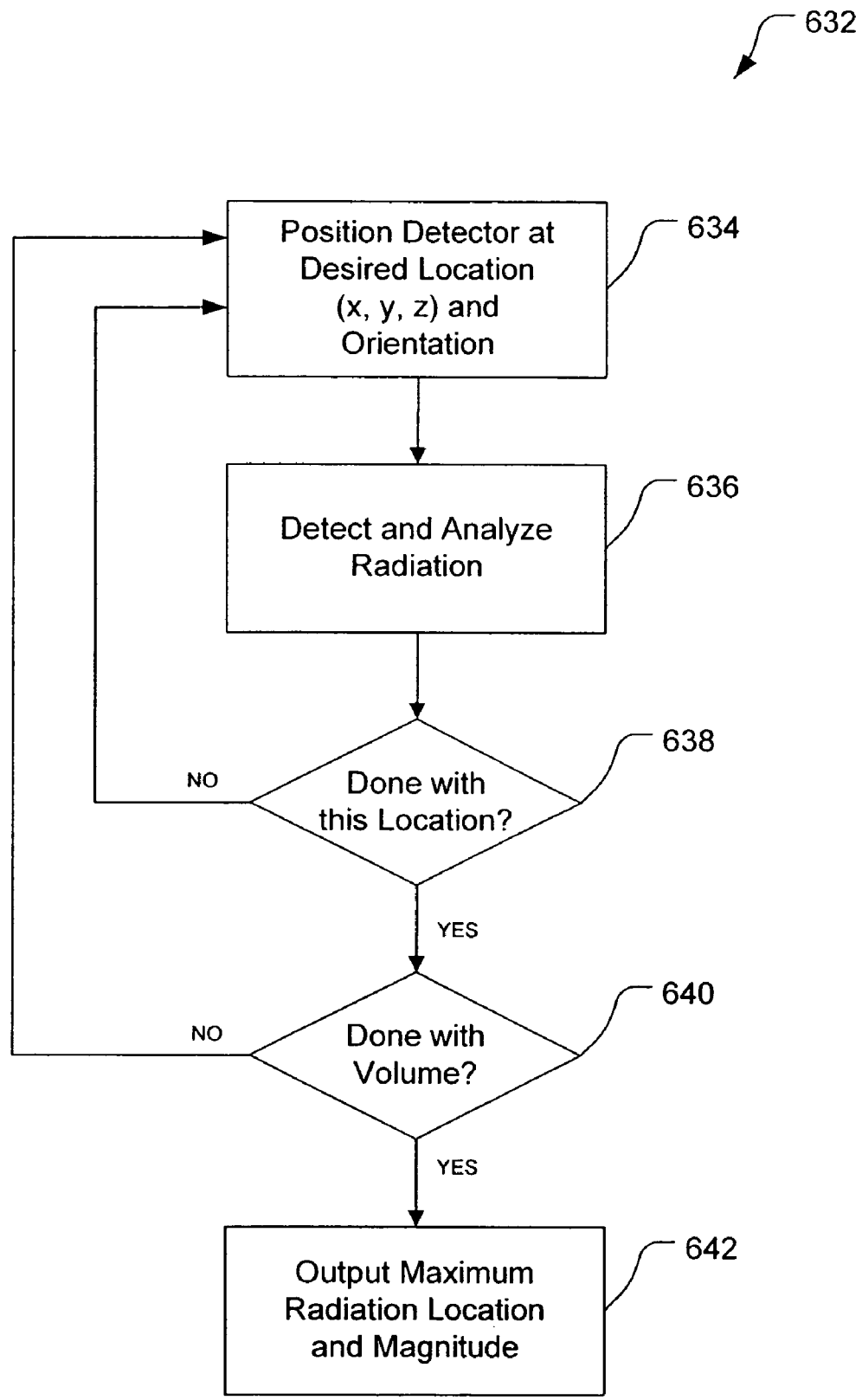
FIG. 15 is a block flow diagram of a process of determining actual radiation distribution values using the system shown in FIG. 14.

In operation, referring to FIG. 15, with further reference to FIG. 14, a process 632 for determining a location and/or magnitude of maximum radiation strength in the volume 620 using the system 610 includes the stages shown. The process 632, however, is exemplary only and not limiting. The process 632 may be altered, e.g., by having stages added, removed, or rearranged. For example, stage 634 discussed below could be performed non-simultaneously.

At stage 632, the controller 618 actuates the robotic arm 614 to position and orient the detector 616 at a desired three-dimensional location in the volume 620. The controller 618 may cause the arm 614 to position the detector 616 at a location that is expected to yield the maximum detected radiation in the volume 620. For example, the position may be on a collimator-defined geometric central axis for a Gamma Knife radiating device 612 or at an expected maximum dose point of a linear accelerator beamlet. The controller 618 also actuates the robotic arm 614 to orient the detector 616 at a desired orientation, e.g., relative to the radiating device 612. The controller 618 may cause the arm 614 to orient the detector 616 in an orientation that is expected to yield the maximum detected radiation for the current detector position. For example, the orientation may be such that the stem or charged central pin of a cylindrical ion chamber is perpendicular to the expected central axis of a beam from the radiating device 612. The positioning and orienting may be done concurrently, e.g., by adjusting orientation while moving to a new location, or may be done independently (e.g., by moving to a new location while keeping the orientation constant or by adjusting the orientation while keeping the location, e.g., of the center of the detector 616, constant).

At stage 636, the radiation detector 616 detects radiation from the radiating device 612 and the controller 618 stores and analyzes the detected radiation. If this is not the first orientation, the controller 618 compares the currently detected radiation amount with previously detected amounts from other orientations.

At stage 638, the controller 618 determines from the detected radiation and from previously detected radiation values whether the current orientation provides the maximum detected radiation for the current position. If more orientations are to be tried, then the process 632 returns to stage 634. If the maximum has been determined, or for any other reason no more orientations are to be tried (e.g., all desired orientations tried), then the process 632 proceeds to stage 640.

At stage 640, the controller 618 determines whether more positions of the detector 616 are to be tried. The controller 618 compares radiation values from the various positions used to determine the maximum detected radiation in the volume 620. If more positions of the detector 616 are to be tried, then the process 632 returns to stage 634. If the maximum detected radiation of the volume 620 has been determined, or no more positions are otherwise to be tried (e.g., all desired positions tried), then the process 632 proceeds to stage 642 where the controller 618 outputs the location and/or magnitude of the maximum detected radiation. These values may be "output" to memory that may be part of the controller 618, or to a separate device such as the treatment planning system 624 as indicated by line 622, e.g., for adjustment of the treatment plan.

As another example, as described with respect to FIG. 2, the controller 42 disposes the radiation detector 28 within the radiation field of the spatial volume and moves the radiation detector within the radiation field of the spatial volume. The controller 42, as described, provides for automatic positioning of the detector 28 within the radiation field 22. A radiation therapist can also manually position the radiation detector 28 within the radiation field 22 using the positioning device 30.

In another example, as described, the system 10 allows for detection of a variance between the location of a determined radiation profile compared to a pre-determined or preset radiation profile location. However, the system 10 also provides for detection regarding changes in the shape of the radiation profile 26 over time. For example, the Gamma Knife, as described, includes 201 cobalt-60 sources that have a half-life of 5.3 years. As the strength of the sources 38 decreases over time, the radiation profile 26 can also change over time, as caused by the decrease in the strength of the radiation sources 38. In such a case, by comparing a determined radiation profile with a pre-established radiation profile, such as provided by the manufacturer, variances in the shape of the radiation profile 26 as caused by a decrease in the strength of the radiation sources can be detected. Such variance can indicate a the need to replace the radiation sources 38 with stronger sources or the need to modify or conform the radiation treatment based upon the determined variance.

In another example, FIG. 9 illustrates controller 42 determining two radiation profiles 26-1, 26-2 for the radiation fields 22 produced by the linear accelerator 100 at two corresponding gantry arm positions 106-1, 106-2. However, the controller 42 can determine any number of radiation profiles 26 corresponding to various positions of the gantry arm 104 relative to the stage 102.

In another example, the positioning device 30, as described above, allows for three-dimensional positioning of the radiation detector 28 within the spatial volume 24 relative to the radiating device 20. In another arrangement, the phantom 68 encompasses the radiation detector 28. The positioning device 30 can three-dimensionally position the combination of the radiation detector 28 and phantom 68 within the spatial volume 24, relative to the radiating device 20.

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Other embodiments of the invention include a computer system, such as a computerized device or other device configured with software and/or circuitry to process and perform operations discussed herein. In such embodiments, the device, such as a controller may include at least one communications interface (e.g., a radiation detector and 3D positioning device interface), a memory (e.g., one or more forms of computer-readable media), a processor and an interconnection mechanism connecting the communications interface, the processor and the memory. The memory system is encoded with a radiation profile detection application that when performed on the processor, produces a radiation profile detection process that causes the computer system to control the radiation detector and the 3D positioning device to perform appropriate operations.

Further, while the discussion above primarily indicated that the controller 42 conforms treatments based upon detected/determined information, the conforming can be don by other portions of radiation systems according to the invention. For example, a radiation device controller, or a person, e.g., a physicist during calibration and/or quality assurance of radiating devices and/or an oncologist during plan adjustment may conform treatments based upon detected/determined information regarding actual radiation distributions of radiating devices.

What is claimed is:

1. A radiation field detection system for use with a radiating device, the detection system comprising:
   a radiation detector configured to receive radiation and to provide radiation strength indicia of amounts of radiation received;
   a positioning mechanism connected to the radiation detector and configured to physically move the radiation detector;
   a processor coupled to the positioning mechanism and coupled to the radiation detector to receive the radiation strength indicia, the processor being configured to:
      actuate the positioning mechanism to move the radiation detector to desired locations within a radiation field produced by the radiating device;
      analyze the radiation strength indicia from the radiation detector;
      correlate positions of the radiation detector with corresponding amounts of received radiation;
      determine a first location of maximum detected radiation; and
      determine a first relationship between the first location of maximum detected radiation and a second location of maximum radiation; and
   an output port configured to be coupled to a controller that determines an excitation arrangement for the radiating device, wherein the processor is further configured to provide an indication of the first relationship to the output port for conveyance to the controller;
   wherein the second location of maximum radiation is one of (1) an expected location of maximum radiation and (2) a determined location of maximum radiation detected under a second radiation condition that is different than a first radiation condition in effect when the radiation was detected leading to the determination of the first location; and
   wherein the second radiation condition is a different angle of application of radiation by the radiating device, with the radiating device being a linear accelerator.

2. The detection system of claim 1 wherein the radiation detector is an ionization chamber.

3. The detection system of claim 1 wherein the radiation detector is a silicon diode detector that has a detection volume of less than about 0.2 mm$^3$.

4. The detection system of claim 1 wherein the positioning mechanism is configured to move the radiation detector three-dimensionally.

5. A radiation field detection system for use with a radiating device, the detection system comprising:
   a radiation detector configured to receive radiation and to provide radiation strength indicia of amounts of radiation received;
   a positioning mechanism connected to the radiation detector and configured to physically move the radiation detector; and
   a processor coupled to the positioning mechanism and coupled to the radiation detector to receive the radiation strength indicia, the processor being configured to:
      actuate the positioning mechanism to move the radiation detector to desired locations within a radiation field produced by the radiating device;
      analyze the radiation strength indicia from the radiation detector;
      correlate positions of the radiation detector with corresponding amounts of received radiation;
      determine a first location of maximum detected radiation;
      determine a first relationship between the first location of maximum detected radiation and a second location of maximum radiation;
      determine a first magnitude of maximum detected radiation; and
      determine a second relationship between the first magnitude of maximum detected radiation and a second magnitude of maximum radiation; and
   an output port configured to be coupled to a controller that determines an excitation arrangement for the radiating device, wherein the processor is further configured to provide an indication of the magnitude relation to the output port for conveyance to the controller;
   wherein the second magnitude of maximum radiation is one of (1) an expected magnitude of maximum radiation and (2) a determined magnitude of maximum radiation detected under a second radiation condition that is different than a first radiation condition in effect when the radiation was detected leading to the determination of the first location; and
   wherein the second radiation condition is a different angle of application of radiation by the radiating device, with the radiating device being a linear accelerator.

6. A radiation field detection system for use with a radiating device, the detection system comprising:
   an ionization chamber radiation detector configured to receive radiation and to provide, in real time, radiation strength indicia of amounts of radiation received;
   a positioning mechanism connected to the radiation detector and configured to physically move the radiation detector; and
   a processor coupled to the positioning mechanism and coupled to the radiation detector to receive the radiation strength indicia, the processor being configured to:
   actuate the positioning mechanism to move the radiation detector to a desired location within a radiation field produced by the radiating device;
   analyze the radiation strength indicia from the radiation detector in real time;
   correlate positions of the radiation detector with corresponding amounts of received radiation in real time; and
   determine, in real time, a location of maximum detected radiation;
   wherein the processor is configured to use the determined location of maximum detected radiation, knowledge of an excitation plan implemented by the radiating device, and an expected location of maximum radiation to determine a revised excitation plan to be implemented by the radiating device.

7. The detection system of claim 6 wherein the processor is configured to correlate the positions of the radiation detector with corresponding amounts of detected radiation as information regarding the positions and the corresponding amounts of radiation becomes available.

8. The detection system of claim 6 wherein the ionization chamber is a silicon diode ionization chamber that has a detection volume of less than about 0.2 mm$^3$.

9. The detection system of claim 6 further comprising an output port configured to be coupled to a controller that determines an excitation arrangement for the radiating device, wherein the processor is further configured to provide an indication of the location of the maximum detected radiation to the output port for conveyance to the controller.

10. The detection system of claim 6 wherein the processor is configured to iterate the revised excitation plan to be implemented by the radiating device until the determined location of maximum detected radiation is within an acceptable distance from the expected location of maximum radiation.

11. The detection system of claim 6 wherein the processor is configured to actuate the positioning mechanism to initially move the radiation detector to at least one of: (1) a geometric central axis if the radiating device is a Gamma Knife, and (2) an expected maximum radiation location of a linear accelerator beam if the radiating device is a linear accelerator.

12. The detection system of claim 6 wherein the processor is configured to actuate the positioning mechanism to move the radiation detector based on a radiation strength previously detected by the radiation detector.

13. A computer-implemented method of using a radiating device, the method comprising using at least one processor to:
apply radiation from the radiating device in accordance with a first excitation plan;
actuate a positioning mechanism to move a radiation detector, configured to receive radiation and to provide radiation strength indicia of amounts of radiation received, in three dimensions within a volume to provide information regarding radiation strength in the volume from the radiating device;
analyze the radiation strength indicia from the radiation detector;
correlate positions of the radiation detector with corresponding amounts of received radiation;
determine a first location of maximum detected radiation;
determine a first relationship between the first location of maximum detected radiation and a second location of maximum radiation; and
determine a second excitation plan based upon the first relationship.

14. The method of claim 13 further comprising using the at least one processor to iterate the second excitation plan until the first relationship satisfies at least one desired criterion.

15. The method of claim 13 wherein the at least one desired criterion includes that the first relationship indicates a positional variance between the first location and the second location that is less than a threshold variance.

16. The method of claim 13 wherein the second location of maximum radiation is one of (1) an expected location of maximum radiation and (2) a determined location of maximum radiation detected under a second radiation condition that is different than a first radiation condition in effect when the radiation was detected leading to the determination of the first location.

17. The method of claim 16 wherein the second radiation condition is a different angle of application of radiation by the radiating device, with the radiating device being a linear accelerator.

18. The method of claim 13 further comprising using the at least one processor to:
determine a first magnitude of maximum detected radiation; and
determine a second relationship between the first magnitude of maximum detected radiation and a second magnitude of maximum radiation.

19. The method of claim 18 wherein the second magnitude of maximum radiation is one of (1) an expected magnitude of maximum radiation and (2) a determined magnitude of maximum radiation detected under a second radiation condition that is different than a first radiation condition in effect when the radiation was detected leading to the determination of the first location.

20. The method of claim 19 wherein the second radiation condition is a different angle of application of radiation by the radiating device, with the radiating device being a linear accelerator.

21. A radiation field detection system for use with a radiating device, the detection system comprising:
a radiation detector configured to receive radiation and to provide radiation strength indicia of amounts of radiation received;
a positioning mechanism connected to the radiation detector and configured to physically move the radiation detector;
a processor coupled to the positioning mechanism and coupled to the radiation detector to receive the radiation strength indicia, the processor being configured to:
actuate the positioning mechanism to move the radiation detector to a desired location within a radiation field produced by the radiating device;
actuate the positioning mechanism to alter an orientation of the radiation detector relative to the radiating device while at the desired location;
analyze the radiation strength indicia from the radiation detector while in different orientations relative to the radiating device while at the desired location; and
determine a desired orientation of the radiation detector for the desired location such that artifacts are reduced.

22. The detection system of claim 21 wherein the processor is further configured to:
correlate positions of the radiation detector with corresponding radiation amounts; and
determine a location of the radiation detector corresponding to a highest amount of detected radiation.

23. The detection system of claim 21 wherein the processor is configured to actuate the positioning mechanism to initially orient the radiation detector to have a central axis of a radiation beam from the radiating device be substantially perpendicular to a stem of the radiation detector.

24. The radiation detector of claim 21 wherein the processor is configured to determine the desired position such that alteration of the orientation of the radiation detector in any direction results in a decrease in detected radiation.

* * * * *